(12) United States Patent
Hashimoto et al.

(10) Patent No.: US 7,981,525 B2
(45) Date of Patent: Jul. 19, 2011

(54) NAPHTHALENE COMPOUND AND ORGANIC LIGHT-EMITTING DEVICE USING THE COMPOUND

(75) Inventors: Masashi Hashimoto, Tokyo (JP); Hironobu Iwawaki, Yokohama (JP); Satoshi Igawa, Fujisawa (JP); Takao Takiguchi, Chofu (JP); Shinjiro Okada, Kamakura (JP)

(73) Assignee: Canon Kabushiki Kaisha, Tokyo (JP)

( * ) Notice: Subject to any disclaimer, the term of this patent is extended or adjusted under 35 U.S.C. 154(b) by 584 days.

(21) Appl. No.: 12/042,919

(22) Filed: Mar. 5, 2008

(65) Prior Publication Data

US 2008/0224603 A1    Sep. 18, 2008

(30) Foreign Application Priority Data

Mar. 12, 2007   (JP) ................. 2007-062188

(51) Int. Cl.
   *H05B 33/14*   (2006.01)
   *C07C 211/43*   (2006.01)
   *C07D 471/22*   (2006.01)
(52) U.S. Cl. .......... 428/690; 428/917; 313/504; 257/40; 585/26; 546/43; 564/426
(58) Field of Classification Search .......... None
   See application file for complete search history.

(56) References Cited

U.S. PATENT DOCUMENTS

| 6,861,163 | B2 | 3/2005 | Cheng et al. ............ 428/690 |
| 2004/0137270 | A1 | 7/2004 | Seo et al. ............ 428/690 |
| 2004/0209118 | A1 * | 10/2004 | Seo et al. ............ 428/690 |
| 2006/0014046 | A1 | 1/2006 | Wang et al. ............ 428/690 |
| 2008/0007161 | A1 | 1/2008 | Kamatani et al. ............ 313/504 |
| 2008/0124577 | A1 | 5/2008 | Saitoh et al. ............ 428/704 |

FOREIGN PATENT DOCUMENTS

| EP | 1690912 A1 * | 8/2006 |
| JP | 2004-139957 | 5/2004 |
| JP | 2004-204238 | 7/2004 |
| JP | 2004-281390 | 10/2004 |
| JP | 2005068087 A * | 3/2005 |
| JP | 2006-045503 | 2/2006 |
| WO | WO 2004/078872 A2 | 9/2004 |
| WO | WO 2008111540 A1 * | 9/2008 |
| WO | WO 2008111543 A1 * | 9/2008 |

OTHER PUBLICATIONS

Machine translation of JP2004-281390. Date of publication: Oct. 7, 2004.*
Suzuki et al. Synthetic Metals 2004, 143, 89-96. Year of publication: 2004.*
Machine translation of JP2005-068087. Date of publication: Mar. 17, 2005.*

* cited by examiner

*Primary Examiner* — Dawn L. Garrett
*Assistant Examiner* — Andrew K Bohaty
(74) *Attorney, Agent, or Firm* — Fitzpatrick, Cella, Harper & Scinto

(57) ABSTRACT

There is provided an organic light-emitting device having an optical output with a high efficiency and a high luminance, and having good durability. The organic light-emitting device includes an anode, a cathode, and a layer including an organic compound interposed between the anode and the cathode, in which the layer contains a naphthalene compound represented by the general formula (1):

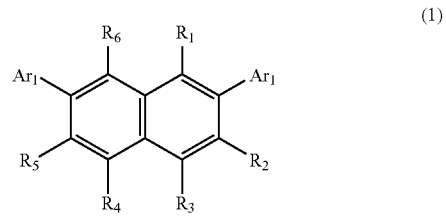

wherein $Ar_1$'s each represent a substituted or unsubstituted fused ring aromatic hydrocarbon group having four or more rings.

3 Claims, 3 Drawing Sheets

NAPHTHALENE COMPOUND AND ORGANIC LIGHT-EMITTING DEVICE USING THE COMPOUND

BACKGROUND OF THE INVENTION

1. Field of the Invention

The present invention relates to a naphthalene compound and a light-emitting device using the compound.

2. Description of the Related Art

Recent progress of an organic light-emitting device is remarkable, and the characteristics of the device enable a thin and light weight light-emitting device with a high luminance at a low applied voltage, a variety of emission wavelengths, and a high-speed responsivity. From this fact, it is suggested that the device have potential to find use in a wide variety of applications.

However, in the present circumstances, an optical output with a higher luminance or a higher conversion efficiency is needed. In addition, the organic light-emitting device still involves a large number of problems in terms of durability such as a change over time due to long-term use and degradation due to an atmospheric gas containing oxygen, moisture or the like. Further, when the application of the device to a full-color display or the like is taken into consideration, the emission of blue, green, or red light with good color purity is needed. However, these problems have not been sufficiently solved yet.

In addition, a large number of aromatic compounds and fused ring aromatic compounds have been researched because of the potential of each of the compounds to serve as a fluorescent organic compound to be used in, for example, an electron-transporting layer or a light-emitting layer. However, it is hard to say that a compound capable of sufficiently satisfying emission luminance and durability has been obtained.

The case where any such aromatic compound or fused ring aromatic compound is used as a component for an organic light-emitting device is described in, for example, each of Japanese Patent Applications Laid-Open No. 2004-281390, No. 2006-045503, No. 2004-139957, No. 2004-204238, and International Publication No. WO2004/078872. Each of Japanese Patent Applications Laid-Open No. 2004-281390, No. 2006-045503, No. 2004-139957, and No. 2004-204238 discloses, as a component for an organic light-emitting device, a compound containing a naphthalene skeleton having a fused ring aromatic group at each of the 2- and 7-positions thereof. Japanese Patent Application Laid-Open No. 2004-281390 discloses the application of a material having a tricyclic fused heterocyclic group to an organic light-emitting device. Japanese Patent Application Laid-Open No. 2006-045503 discloses the application of a material containing a naphthalene skeleton having a substituent at each of the 2- and 7-positions thereof as a core to an organic light-emitting device. In addition, each of Japanese Patent Applications Laid-Open No. 2004-139957 and No. 2004-204238, and International Publication No. WO2004/078872 discloses the application of a compound having two fused tetracyclic aromatic hydrocarbon groups at the 1- and 5-positions or 2- and 6-positions thereof on a naphthalene ring to an organic light-emitting device.

In order to apply an organic light-emitting device to a display apparatus such as a display, it is necessary to secure an optical output with a high efficiency and a high luminance, and, at the same time, to secure high durability sufficiently. However, it cannot be said that the technologies described in any one of Japanese Patent Applications Laid-Open No. 2004-281390, No. 2006-045503, No. 2004-139957, and No. 2004-204238, and International Publication No. WO2004/078872 can sufficiently solve those problems.

SUMMARY OF THE INVENTION

In view of the foregoing, an object of the present invention is to provide an organic light-emitting device having an optical output with a high efficiency and a high luminance, and having good durability. Another object of the present invention is to provide a light-emitting device that can be easily produced at a relatively low cost.

The naphthalene compound of the present invention is represented by the following general formula (1):

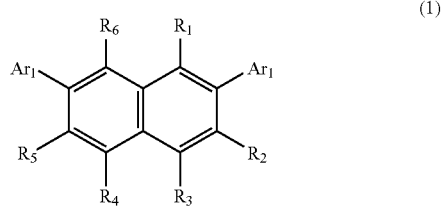

wherein $Ar_1$'s each represent a substituted or unsubstituted fused ring aromatic hydrocarbon group having four or more rings, and $R_1$, $R_2$, $R_3$, $R_4$, $R_5$, and $R_6$ each represent, independently of one another, a hydrogen atom, a halogen atom, an alkyl group having 1 to 20 carbon atoms, a substituted or unsubstituted aryl group, or a substituted or unsubstituted heterocyclic group.

According to the present invention, there can be provided an organic light-emitting device having an optical output with a high efficiency and a high luminance, and having good durability. In addition, the light-emitting device of the present invention is also an excellent display device.

Further features of the present invention will become apparent from the following description of exemplary embodiments with reference to the attached drawings.

DESCRIPTION OF THE EMBODIMENTS

Figure 1:
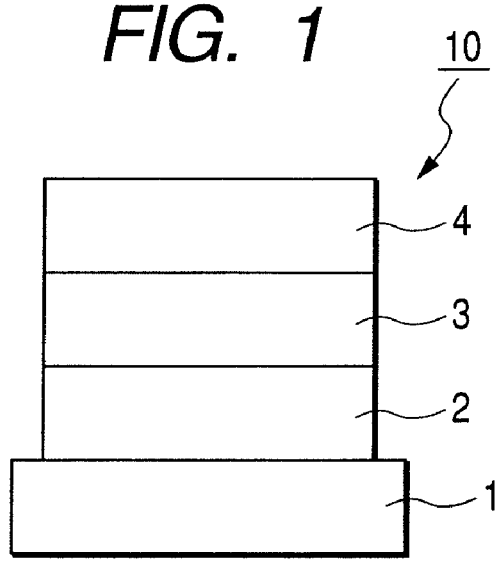
FIG. 1 is a cross-sectional view illustrating a first embodiment of the organic light-emitting device of the present invention.

Hereinafter, the present invention will be described in detail. First, the naphthalene compound of the present invention will be described. The naphthalene compound of the present invention is represented by the following general formula (1).

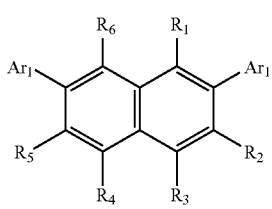

(1)

In the formula (1), $Ar_1$'s each represent a substituted or unsubstituted fused ring aromatic hydrocarbon group having four or more rings.

$Ar_1$'s each preferably represent a fused ring aromatic hydrocarbon group having four (4) to seven (7) rings from the viewpoints of the carrier transporting ability and the energy gap. $Ar_1$'s each more preferably represent a fused ring aromatic hydrocarbon group with four (4) or five (5) rings. $Ar_1$'s each particularly preferably represent a fused ring aromatic hydrocarbon group with four (4) rings.

Examples of the fused ring aromatic hydrocarbon group having four or more rings represented by each of $Ar_1$'s include a pyrenyl group, a fluoranthenyl group, a benzofluoranthenyl group, a tetracenyl group, a pentacenyl group, a triphenylenyl group, a perylenyl group, a chrysenyl group, a benzoanthryl group, a benzophenanthryl group, a pentaphenyl group, a picenyl group, a benzopyrenyl group, a hexacenyl group, a dibenzochrysenyl group, a tetrabenzoanthryl group, a cholonyl group, and a corannulenyl group, although these are merely representative examples and the present invention is not limited to the examples.

Of those substituents, a pyrenyl group, a fluoranthenyl group, a benzofluoranthenyl group, and a triphenylenyl group are preferable from the viewpoints of the conductivity and the energy gap, with a fluoranthenyl group and a pyrenyl group being particularly preferable.

The substituent which the fused ring aromatic hydrocarbon groups with four or more rings may have is, for example, a halogen atom, an alkyl group having 1 to 20 carbon atoms, a substituted amino group, a substituted or unsubstituted aryl group, or a substituted or unsubstituted heterocyclic group, though these are merely representative examples and the present invention is not limited to the examples.

Preferable examples of the halogen atom include a fluorine atom, a chlorine atom, and a bromine atom. When an organic light-emitting device is produced by a vacuum evaporation method, a fluorine atom is particularly preferable.

Examples of the alkyl group having 1 to 20 carbon atoms include a methyl group, an ethyl group, an n-propyl group, an isopropyl group, an n-butyl group, a tert-butyl group, an octyl group, and a cyclohexyl group. In addition, when the alkyl group has two or more carbon atoms, one methylene group or two or more non-adjacent methylene groups in the alkyl group may be replaced by —O— so that, for example, a methoxy group or an ethoxy group is formed. Further, hydrogen atom(s) in the alkyl group may be substituted with a fluorine atom(s) so that, for example, a trifluoromethyl group is formed.

Of those alkyl groups, a methyl group, a tert-butyl group, a cyclohexyl group, and a trifluoromethyl group are preferable from the viewpoints of the conductivity and the glass transition temperature, a methyl group, a tert-butyl group, and a trifluoromethyl group are more preferable, and a methyl group and a tert-butyl group are still more preferable.

From the viewpoints of the conductivity and the glass transition temperature, examples of the substituted amino group preferably include a dimethylamino group, a diphenylamino group, and a ditolylamino group, particularly preferably a diphenylamino group.

Examples of the aryl group which may have a substituent include a phenyl group, a biphenyl group, a terphenyl group, a fluorenyl group, a naphthyl group, a fluoranthenyl group, an anthryl group, a phenanthryl group, a pyrenyl group, a tetracenyl group, a pentacenyl group, a triphenylenyl group, and perylenyl group.

From the viewpoint of the sublimation property, a phenyl group, a fluoranyl group, and a naphthyl group are preferred. A phenyl group is more preferred.

Examples of the heterocyclic group which may have a substitutent include a thienyl group, a pyrrolyl group, a pyridyl group, a pyrazyl group, a pyrimidyl group, a pyridazinyl group, a quinolynyl group, an isoquinolynyl group, a phenanthridinyl group, an acrydinyl group, a naphthyridinyl group, a quinoxalinyl group, quinazolinyl group, a cinnolinyl group, a phthalazinyl group, a phenanthrolyl group, a phenazinyl group, a dibenzofuranyl group, a dibenzothiophenyl group, a carbazolyl group, a benzofuranyl group, a benzothiophenyl group, an indolyl group, a cycloacyl group, a benzoimidazolyl group, a benzothiazolyl group, and a benzothiadiazolyl group.

A pyridyl group is preferable from the viewpoint of the sublimation property.

Although the substituent which each of the above-mentioned aryl group and heterocyclic group may have is not particularly limited, the substituent is preferably a halogen atom, an alkyl group having 1 to 20 carbon atoms, or a substituted amino group. When the alkyl group has 2 or more carbon atoms, one methylene group, or two or more non-adjacent methylene groups in the alkyl group may be replaced by —O—. In addition, hydrogen atom(s) in the alkyl group may be substituted with fluorine atom(s). Specific examples of each of the halogen atom, the alkyl group, and the substituted amino group are the same as the specific examples of each of the halogen atom, the alkyl group, and the substituted amino group described above as a preferred substituent for $Ar_1$'s.

Of those substituents, a fluorine atom, a trifluoromethyl group, a methyl group, an ethyl group, a tert-butyl group, a methoxy group, a dimethylamino group, and a di-tert-butylamino group are preferable from the viewpoints of the glass transition temperature and the sublimation property, a fluorine atom, a trifluoromethyl group, a methyl group, and a tert-butyl group are more preferable, and a methyl group and a tert-butyl group are particularly preferable.

The substituents which can be introduced into two $Ar_1$'s in the formula (1) are identical to each other. This has the advantage that the production process for the compound can be simplified as compared to that in the case where different substituents are introduced into respective $Ar_1$'s. As a result, the naphthalene compound of the present invention can be produced at a low cost.

In the formula (1), $R_1$, $R_2$, $R_3$, $R_4$, $R_5$, and $R_6$ each represent, independently of one another, a hydrogen atom, a halogen atom, an alkyl group having 1 to 20 carbon atoms, a substituted or unsubstituted aryl group, or a substituted or unsubstituted heterocyclic group.

Examples of the halogen atom represented by each of $R_1$, $R_2$, $R_3$, $R_4$, $R_5$, and $R_6$ include a fluorine atom, a chlorine atom, and a bromine atom. When an organic light-emitting device is produced from the compound by a vacuum evaporation method, a fluorine atom is preferable.

Examples of the alkyl group having 1 to 20 carbon atoms and represented by each of $R_1$, $R_2$, $R_3$, $R_4$, $R_5$, and $R_6$ include a methyl group, an ethyl group, an n-propyl group, an isopropyl group, an n-butyl group, a tert-butyl group, an octyl group, and a cyclohexyl group. When the alkyl group has two or more carbon atoms, one methylene group or two or more non-adjacent methylene groups may be replaced by —O— to be a methoxy group or an ethoxy group, for example. In addition, hydrogen atom(s) in the alkyl group may be substituted with fluorine atom(s) to form a trifluoromethyl group, for example.

Of those, from the viewpoints of the conductivity and the glass transition temperature of the compound, preferred are a methyl group, a tert-butyl group, a cyclohexyl group, and a trifluoromethyl group. More preferred are a methyl group, a tert-butyl group, and a trifluoromethyl group. Still more preferred are a methyl group and a tert-butyl group.

Examples of the aryl group represented by each of $R_1$, $R_2$, $R_3$, $R_4$, $R_5$, and $R_6$ include a phenyl group, a biphenyl group, a terphenyl group, a fluorenyl group, a naphthyl group, a fluoranthenyl group, an anthryl group, a phenanthryl group, a pyrenyl group, a tetracenyl group, a pentacenyl group, a triphenylenyl group, and a perylenyl group. From the viewpoint of the sublimation property of the compound, preferred are a phenyl group, a fluorenyl group, and a naphthyl group. More preferred is a phenyl group.

Examples of the heterocyclic group represented by each of $R_1$, $R_2$, $R_3$, $R_4$, $R_5$, and $R_6$ include a thienyl group, a pyrrolyl group, a pyridyl group, pyrazyl group, a pyrimidyl group, a pyridazinyl group, a quinolynyl group, an isoquinolynyl group, a phenanthridinyl group, an acridinyl group, a naphthyridinyl group, a quinoxalinyl group, quinazolinyl group, a cinnolinyl group, a phthalazinyl group, a phenanthrolyl group, a phenazinyl group, a dibenzofuranyl group, a dibenzothiophenyl group, a carbazolyl group, a benzofuranyl group, a benzothiophenyl group, an indolyl group, a cycloacyl group, a benzoimidazolyl group, a benzothiazolyl group, and a benzothiadiazolyl group. From the viewpoint of the sublimation property, a pyridyl group is preferred.

Incidentally, when the molecular weight of the compound is excessively large, the sublimation temperature of the compound increases, and the probability that the compound thermally decomposes at the time of vacuum evaporation increases. Accordingly, there are cases where the introduction of a large substituent is not preferable.

The substituent which each of the above-mentioned aryl group and heterocyclic group may have is a halogen atom, a substituted amino group, or an alkyl group having 1 to 20 carbon atoms. Of those substituents, a fluorine atom, a trifluoromethyl group, a methyl group, an ethyl group, a tert-butyl group, a methoxy group, a dimethylamino group, and a di-tert-butylamino group are preferable from the viewpoints of the glass transition temperature and the sublimation property of the compound, a fluorine atom, a trifluoromethyl group, a methyl group, and a tert-butyl group are more preferable, and a methyl group and a tert-butyl group are still more preferable.

In the naphthalene compound of the present invention, it is particularly preferable from the viewpoint of the conductivity that a dihedral angle formed between a plane including the naphthalene ring and a plane including $Ar_1$'s is the minimum. Therefore, $R_1$, $R_2$, $R_3$, $R_4$, $R_5$, and $R_6$ each preferably represent a hydrogen atom or fluorine atom having a small atomic radius, and each particularly preferably represent a hydrogen atom having the smallest atomic radius.

The foregoing description about the naphthalene compound of the present invention has focused on the substituents which each of $Ar_1$'s in the formula (1) may have and the substituents $R_1$, $R_2$, $R_3$, $R_4$, $R_5$, and $R_6$ in the formula (1). The naphthalene compound of the present invention particularly preferably has a structure formed only of carbon atoms and hydrogen atoms, out of the specific structures formed including those substituents. This is because it is considered that a molecule of the compound formed only of carbon atoms and hydrogen atoms may further reduce the uptake of, for example, an ionic impurity considered as one possible cause for the energization degradation of an organic light-emitting device, as compared to a compound containing a hetero atom having a lone pair of electrons. The reduction of the inclusion of an ionic impurity prolongs the life of the organic light-emitting device.

The naphthalene compound of the present invention can be synthesized via, for example, the following route.

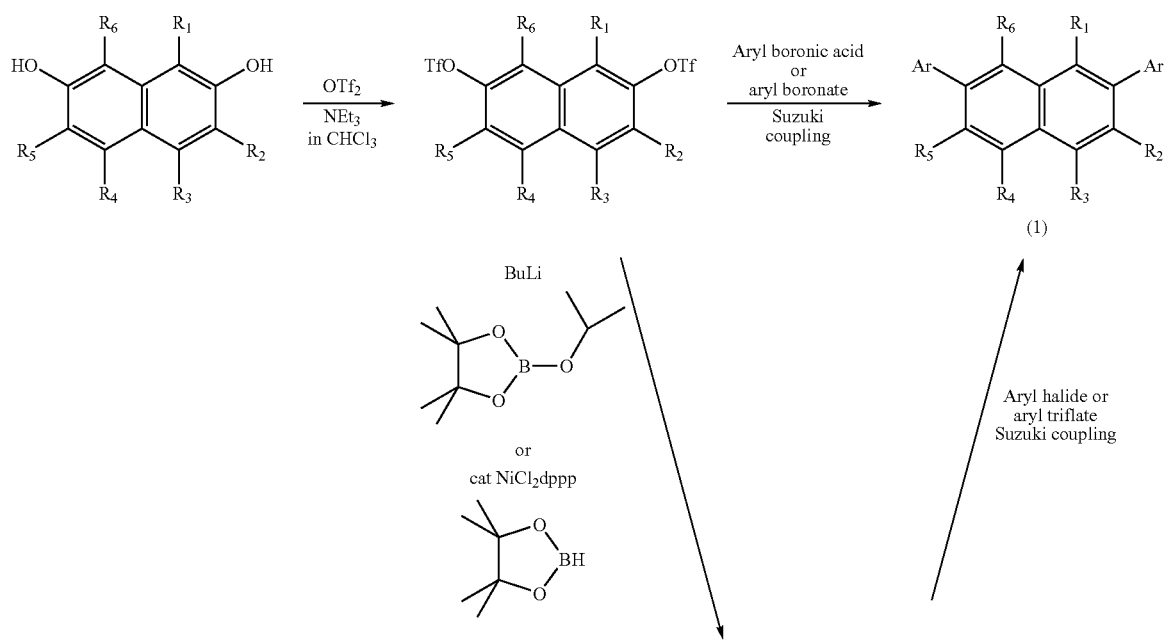

-continued

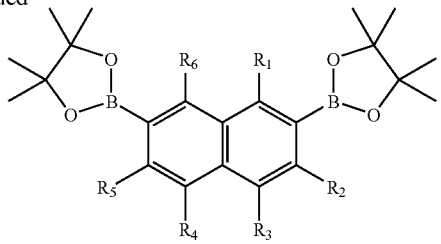

It is desirable that the naphthalene compound of the present invention is purified so sufficiently as to remove impurities. The cause for emission degradation due to energization includes the inclusion of an impurity. When a polymer compound is used as a constituent material of the device, it is difficult to remove an impurity in the polymer, so that the impurity is liable to be contaminated into the device, thereby reducing the life of the device. On the other hand, because the naphthalene compound of the present invention is a single compound, an impurity can be easily removed from the compound by appropriately employing a purification method such as a recrystallization method, a column chromatography method, or a sublimation purification method. Accordingly, the use of the naphthalene compound of the present invention as a constituent material for an organic light-emitting device improves the durability of the organic light-emitting device.

The naphthalene compound of the present invention has identical fused ring aromatic hydrocarbon groups having four or more rings at the 2- and 7-positions of the naphthalene skeleton thereof. In addition, the naphthalene compound of the present invention further has the following three characteristics.

A first characteristic is that the compound has a large molecular weight because the compound has two fused ring aromatic hydrocarbon groups having four or more rings on the naphthalene which is a rigid core. As a result, the naphthalene compound of the present invention has a high glass transition temperature.

Although the cause for the emission degradation due to energization of an organic light-emitting device has not been revealed yet, the degradation is assumed to be related to at least a change in environment such as heat of a light-emitting material due to a light-emitting center material itself or molecules existing around the light-emitting center material. Here, when the thermal stability of the organic thin film in a glass state is high, that is, when the organic compound constituting the organic thin film has a high glass transition point, the above environmental change hardly occurs, which may result in prolongation of the life of the organic light-emitting device. In the naphthalene compound of the present invention, the two fused ring aromatic hydrocarbon groups having four or more rings are introduced into the naphthalene ring. The introduction increases the molecular weight of the compound, and raises the glass transition temperature of the molecule itself of the compound.

A second characteristic is that the naphthalene ring is substituted with the two fused ring aromatic hydrocarbon groups at the positions where no peri position is present. In this case, the planarity of the molecule of the compound may be improve as compared to that in the case where the substituents are introduced into positions where a peri position is present of the naphthalene ring. Thereby, higher carrier transporting ability can be expected to be exhibited.

In order that the drive voltage of the organic light-emitting device is suppressed to a low voltage, the material constituting the organic light-emitting device desirably has a high carrier mobility. The molecule of the naphthalene compound of the present invention can be formed to have a wide π-electron surface by introducing the two fused ring aromatic hydrocarbon groups with four or more rings into the naphthalene ring as a rigid skeleton having a relatively wide π-electron surface. In such a compound having a large π-electron surface, the increase of overlapping of π-electrons between adjacent molecules in the organic film can be expected, which is considered to advantageously contribute to carrier transport. Therefore, the use of the naphthalene compound of the present invention in an organic light-emitting device may be advantageous from the viewpoint of carrier transport as well.

In addition, the present naphthalene compound having the fused ring aromatic hydrocarbon groups introduced into the 2- and 7-positions of the naphthalene ring has no peri position on the naphthalene ring, unlike the case where the groups are introduced into any of the 1-, 4-, 5-, and 8-positions. The introduction of the fused ring aromatic hydrocarbon groups into the 2- and 7-positions where no peri position is present reduces the dihedral angle formed between a plane including the naphthalene ring and a plane including the fused ring aromatic hydrocarbon groups as compared to that in the case where the fused ring aromatic hydrocarbon groups are introduced into any of the 1-, 4-, 5-, and 8-positions. As a result, the planarity of the molecule of the compound improves. As a result, the molecule is expected to have a wide π-electron surface over the entirety of the molecule, which is considered to advantageously contribute to the carrier transport. Here, from the viewpoint of further improvement of the planarity of the molecule, $R_1$, $R_2$, $R_5$, and $R_6$ in the general formula (1) each preferably represent a hydrogen atom or fluorine atom as a substituent having small steric hindrance with $Ar_1$'s, and each particularly preferably represent a hydrogen atom having the smallest atomic radius.

A third characteristic is that the two fused ring aromatic hydrocarbon groups with four or more rings are introduced into such positions that their π-conjugated systems are not linked to each other through the naphthalene ring. As a result, the energy gap can be made larger as compared to that in the case where the two fused ring aromatic hydrocarbon groups are introduced into such positions that their π-conjugated systems are linked to each other through the naphthalene ring.

When the fused ring aromatic hydrocarbon groups are introduced into the 2- and 6-positions at which no peri position is present on the naphthalene ring, the π-conjugated systems of the fused ring aromatic hydrocarbon groups can be linked to each other through the naphthalene ring. On the other hand, when the fused ring aromatic hydrocarbon groups are introduced into the 2- and 7-positions, their π-conjugated systems are not linked to each other through the naphthalene ring. As a result, the naphthalene compound of the present invention having large π-conjugated systems introduced into such substitution positions (the 2- and 7-positions) where the π-conjugated systems are not linked to each other has a larger energy gap than that in the case where the large π-conjugated systems are introduced into such substitution positions (the 2- and 6-positions) where the π-conjugated systems are linked to each other. Incidentally, the term "energy gap" herein employed refers to an energy gap between an HOMO and an LUMO of the molecular orbitals of the compound. Hereinafter, the term "energy gap" has the above defined meaning unless otherwise noted).

Specific examples of the naphthalene compound of the present invention are shown below, although these are merely representative examples and the naphthalene compound of the present invention is not limited to the examples.

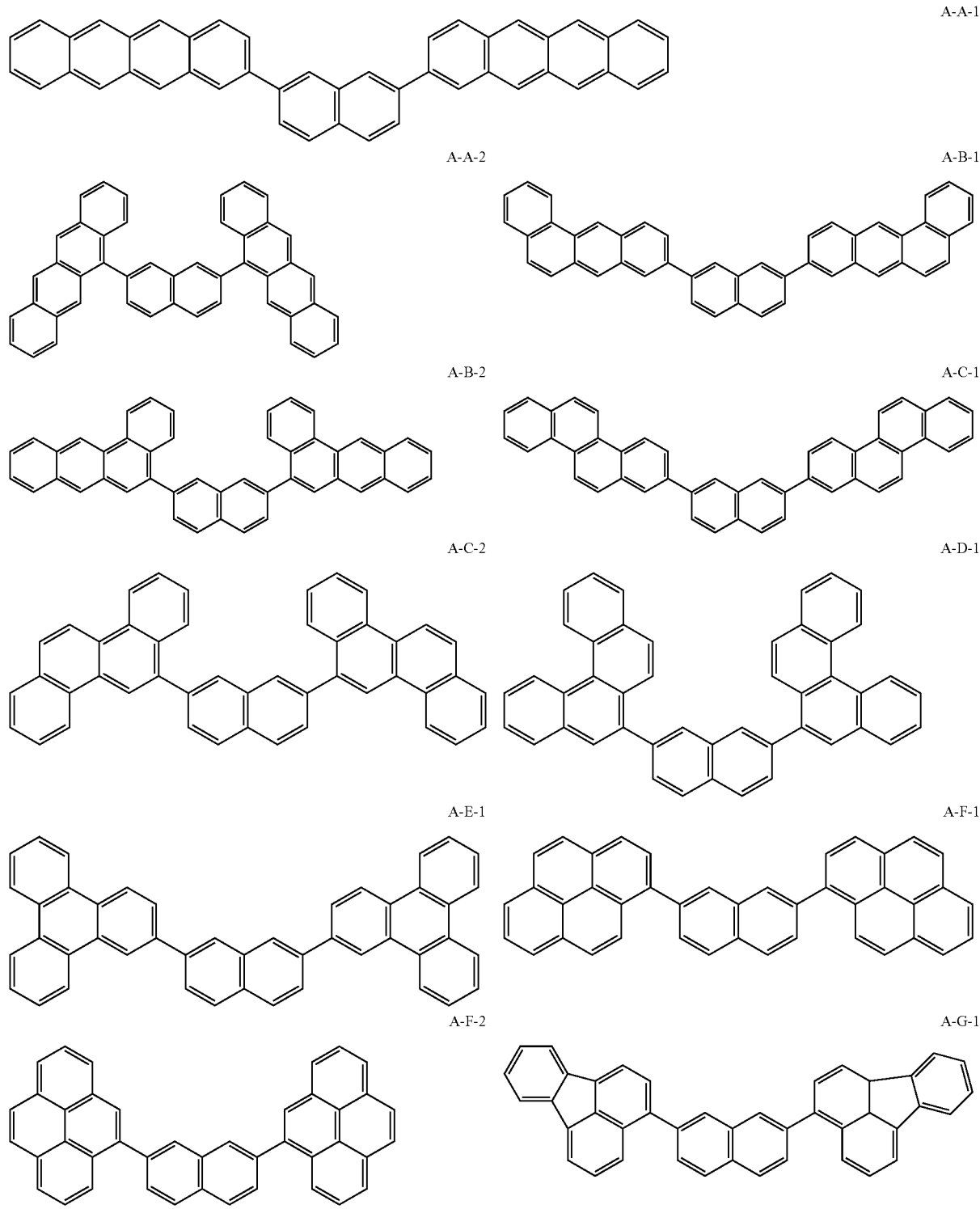

-continued
A-G-2
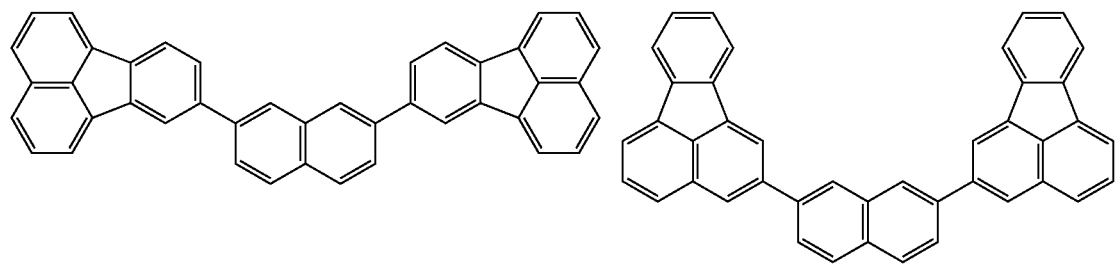
A-G-3
A-G-4
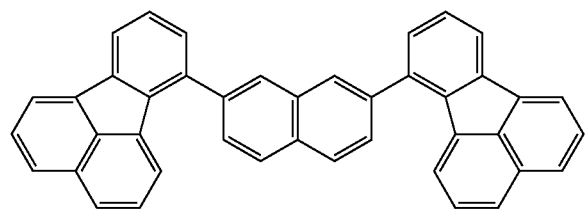
A-H-1
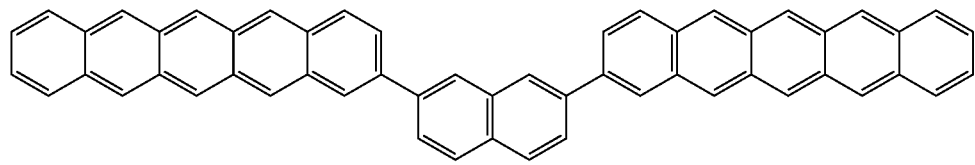
A-H-2
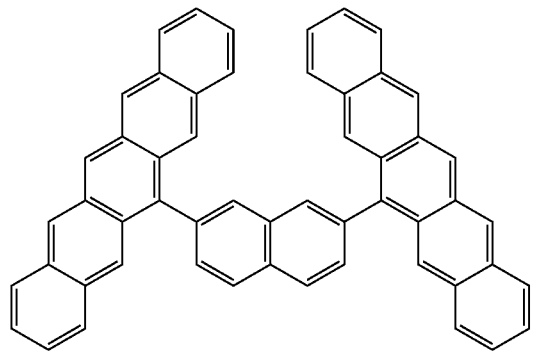
A-I-1
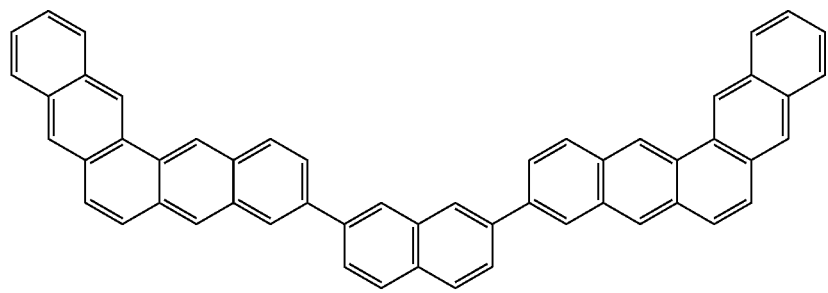
A-I-2
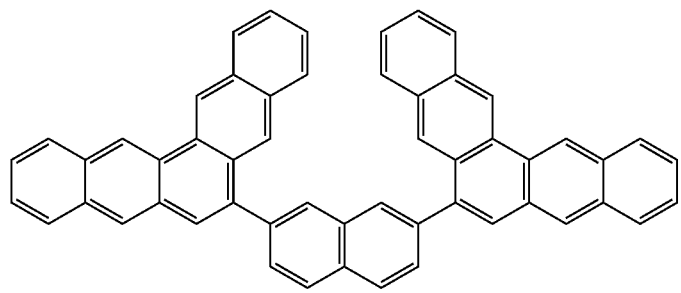

-continued
A-J-1
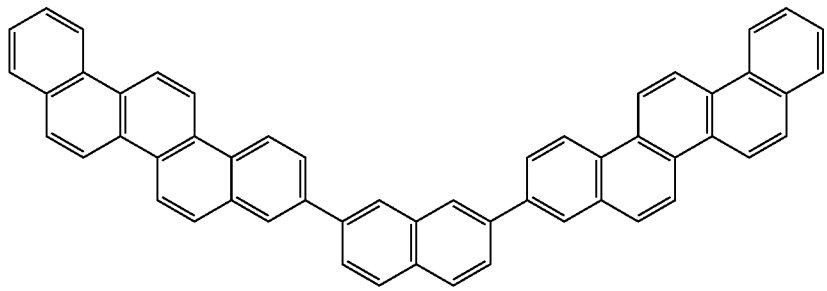
A-J-2
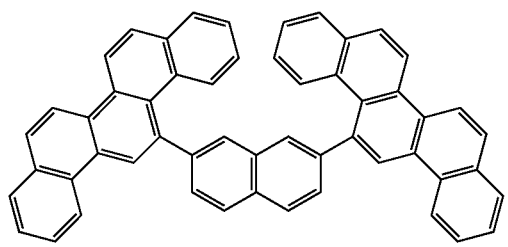
A-K-1
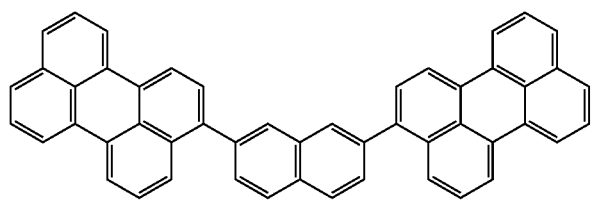
A-L-1
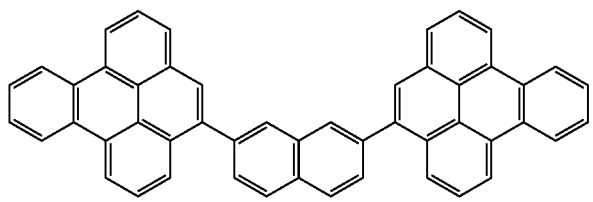
A-L-2
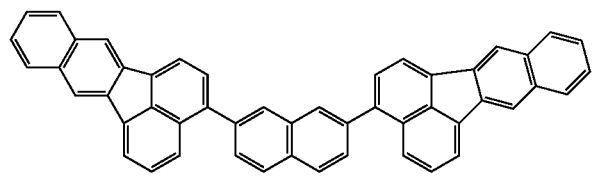
A-M-1
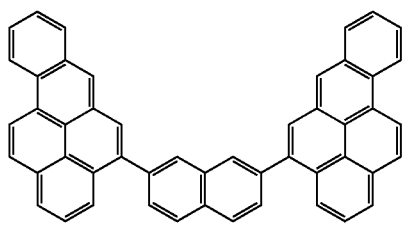
A-N-1
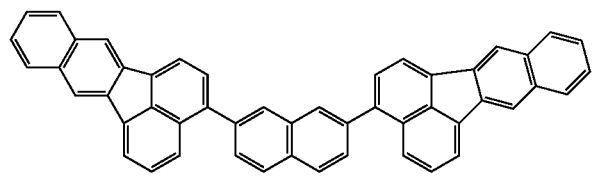
A-N-2
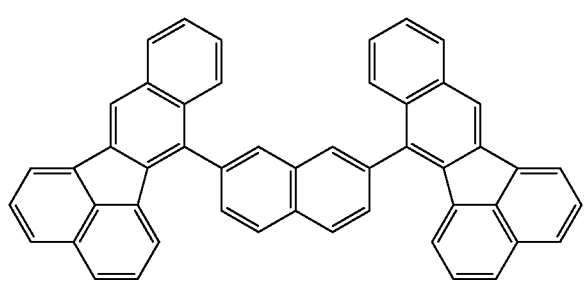
A-O-1
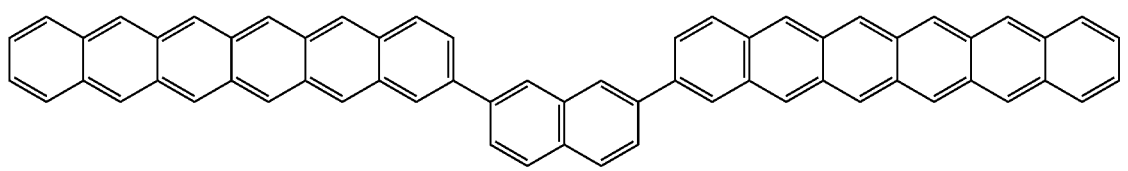

-continued
A-P-1
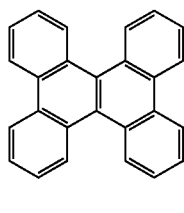
A-P-2
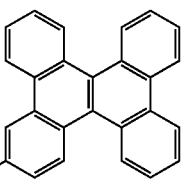
A-Q-1
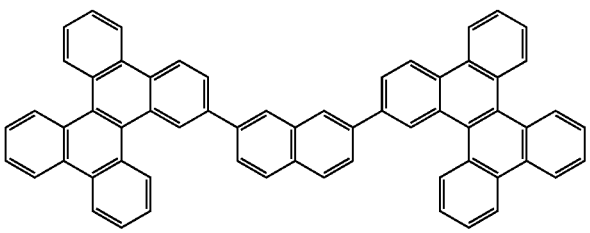
A-R-1
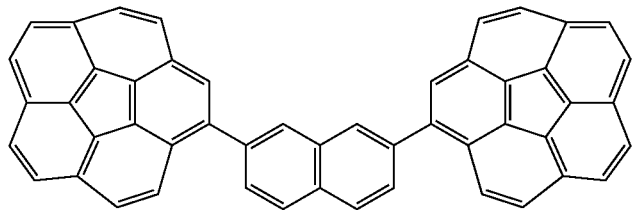
A-S-1
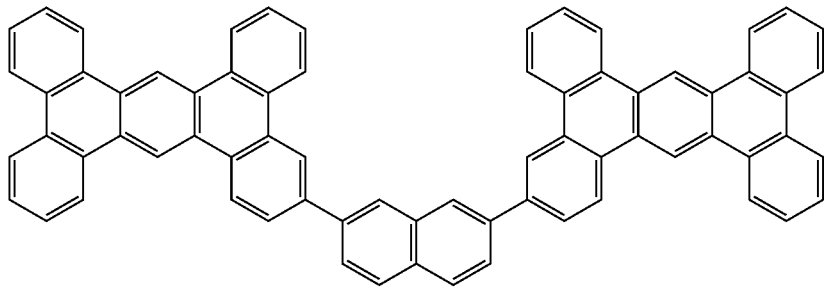
B-A-1
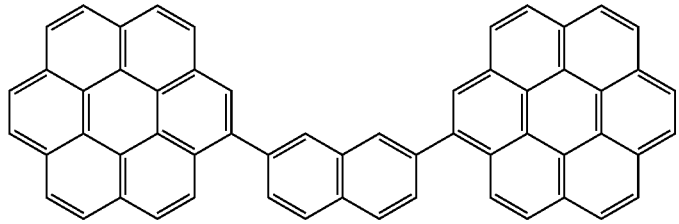
B-A-2
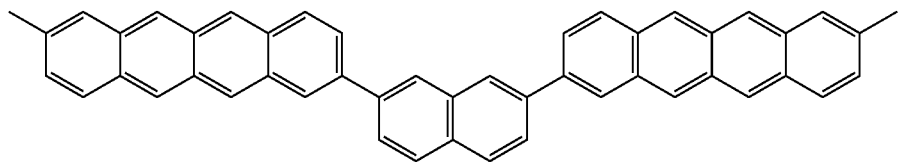
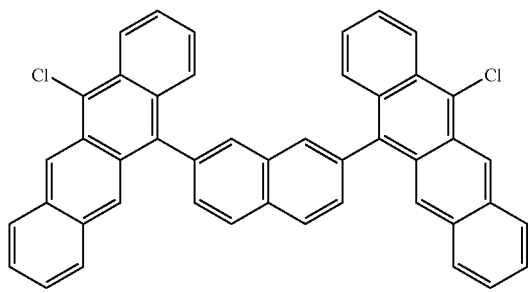

B-B-1
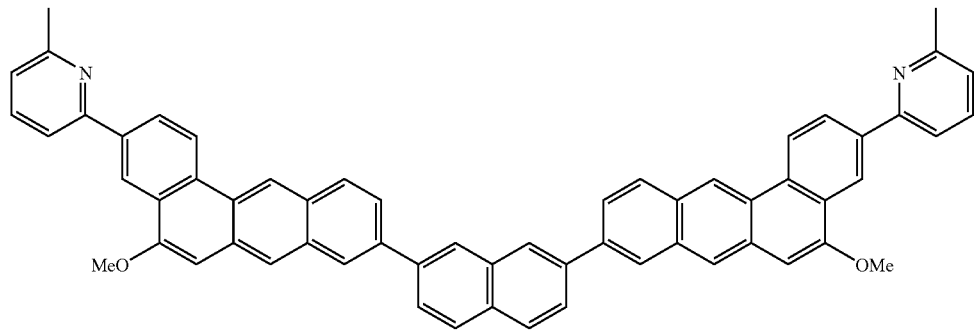
B-B-2
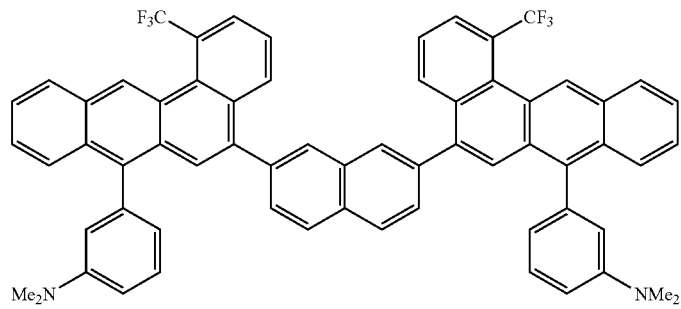
B-C-1
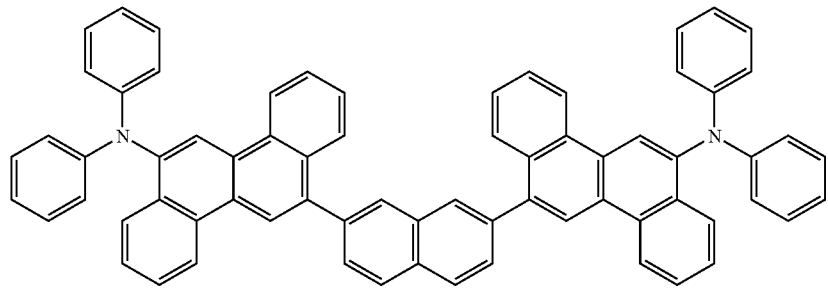
B-C-2
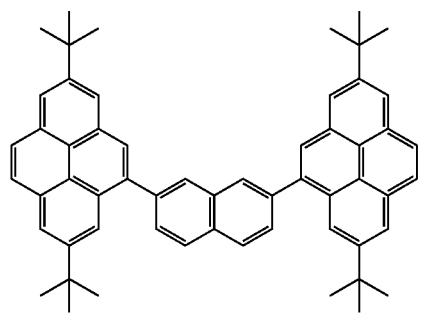
B-F-1
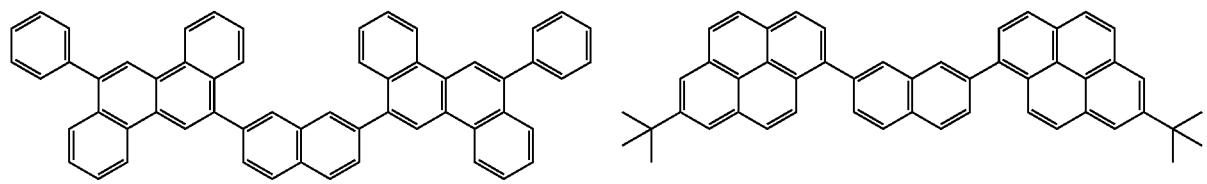
B-F-2
B-F-3
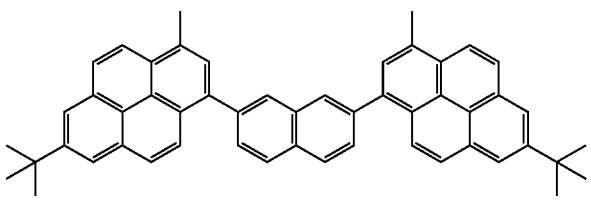

-continued
B-G-1
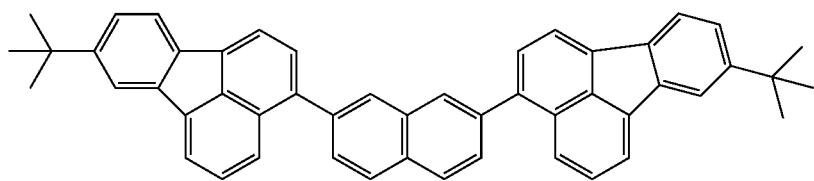
B-G-2
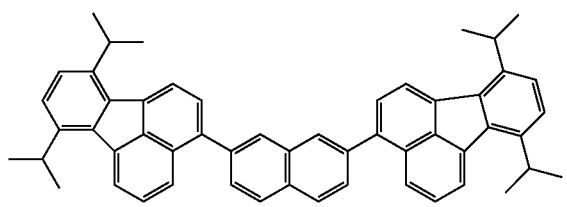
B-G-3
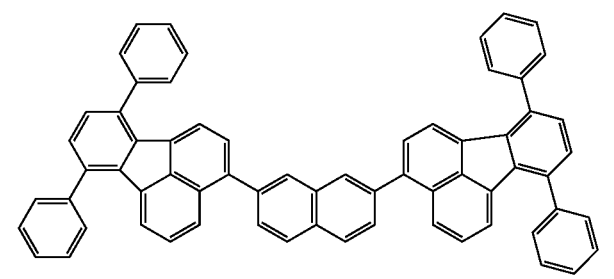
B-G-4
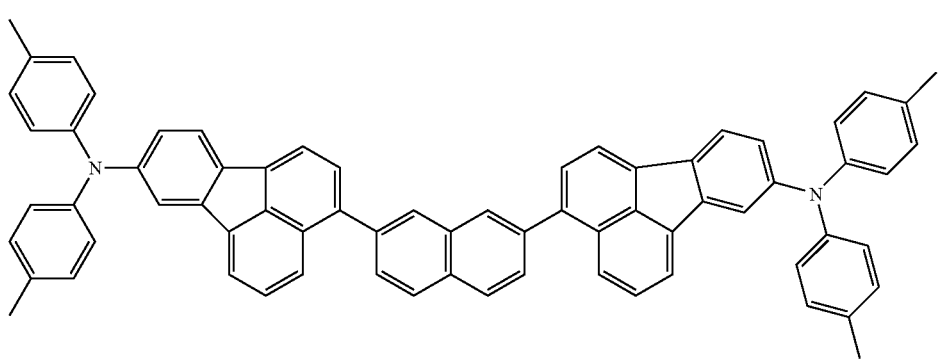
B-G-5
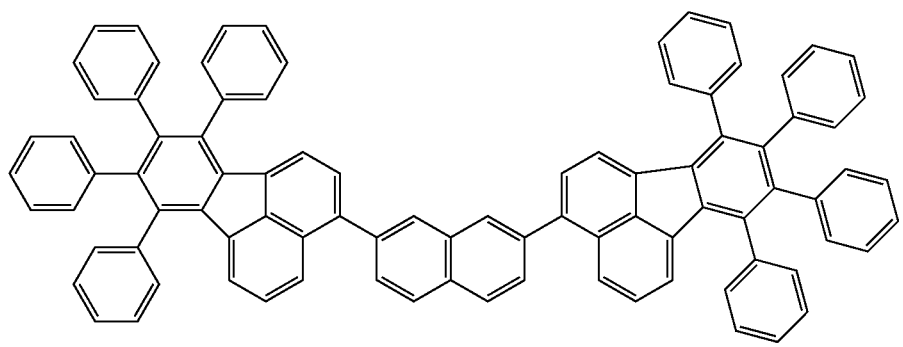
B-K-1
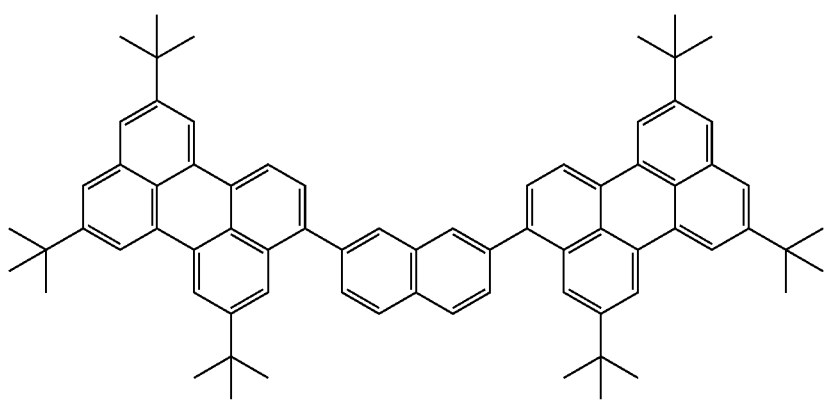

-continued
B-N-1
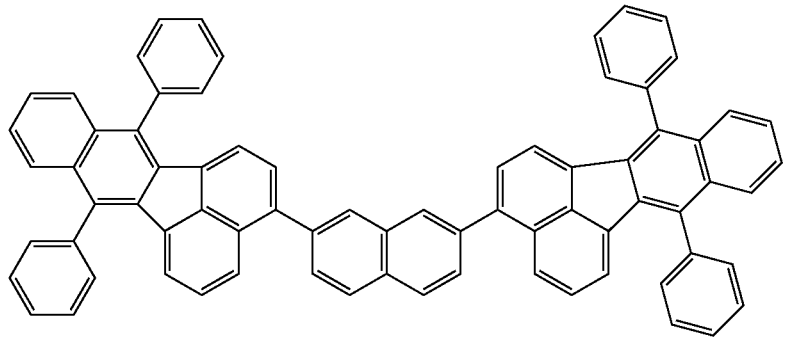
C-C-1
C-E-1
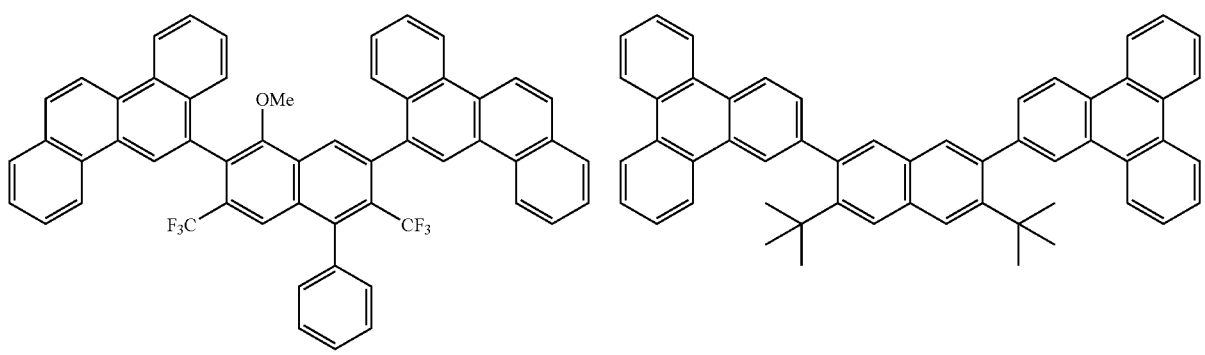
C-F-1
C-F-2
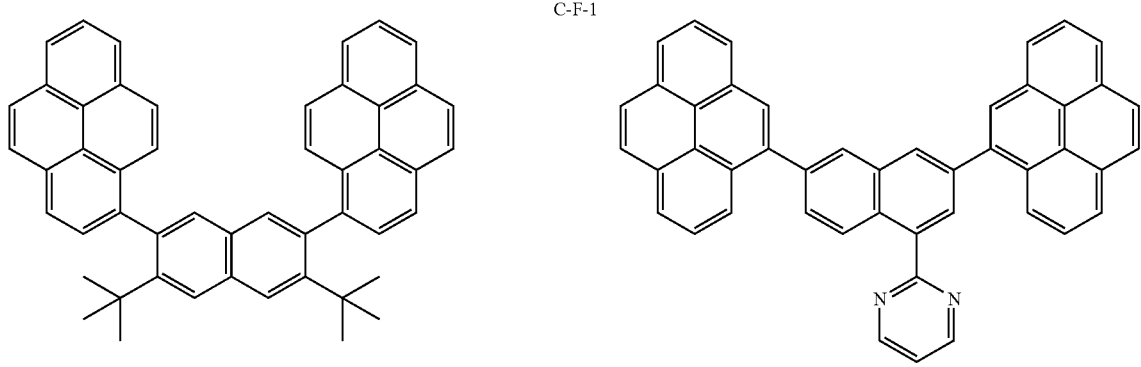
C-G-1
C-G-2
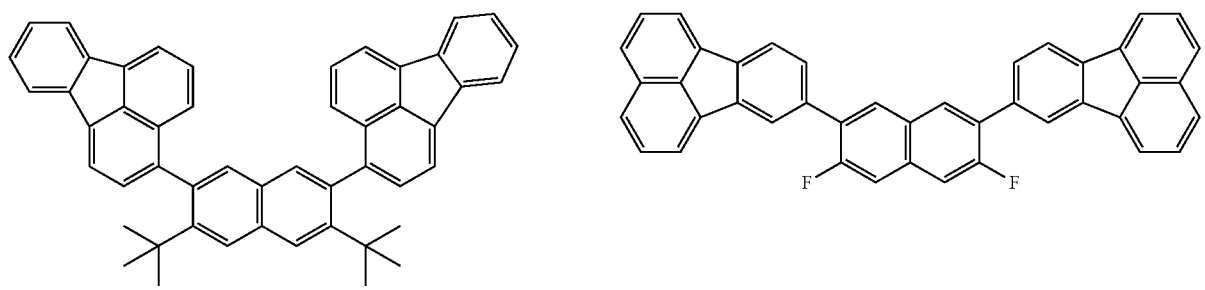

-continued
C-K-1  C-P-1
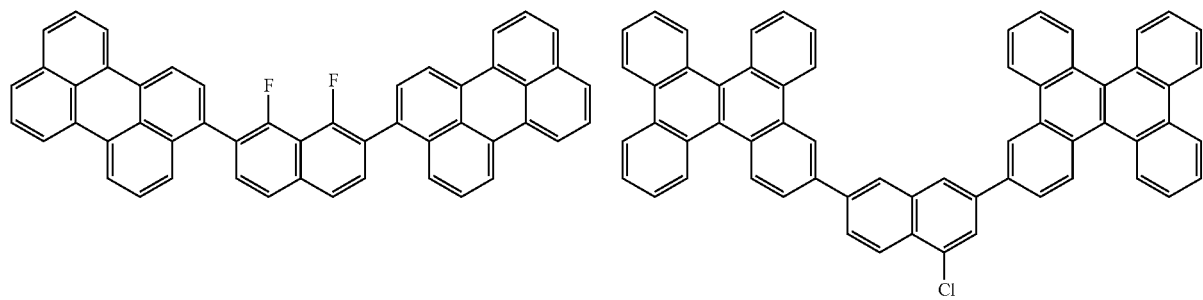
D-F-1  D-F-2
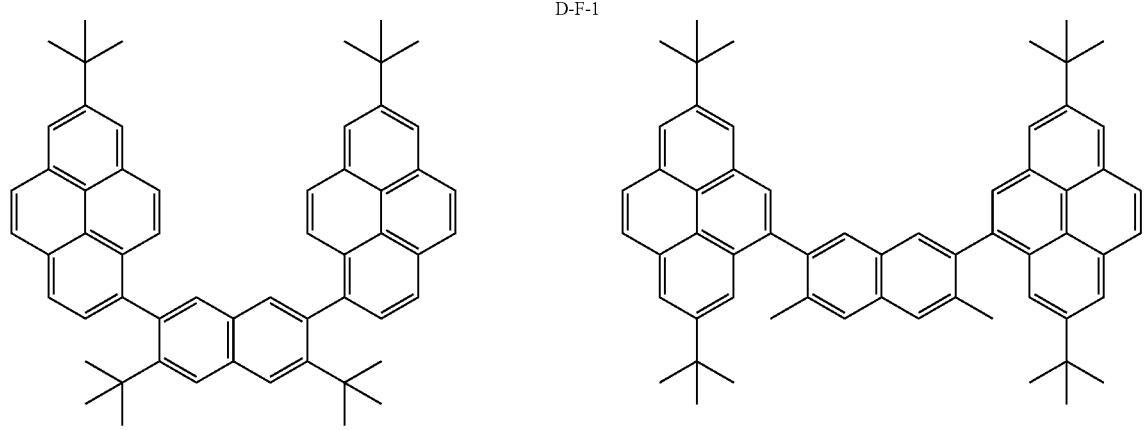
D-F-3
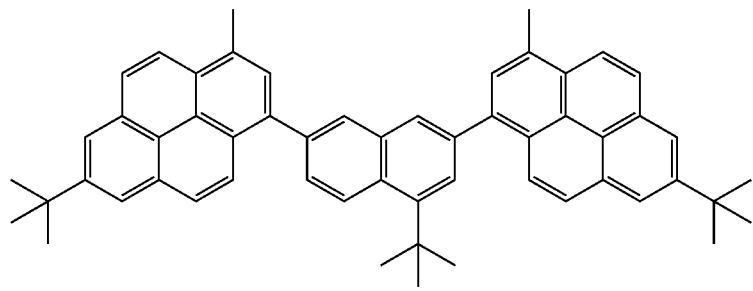
D-G-1
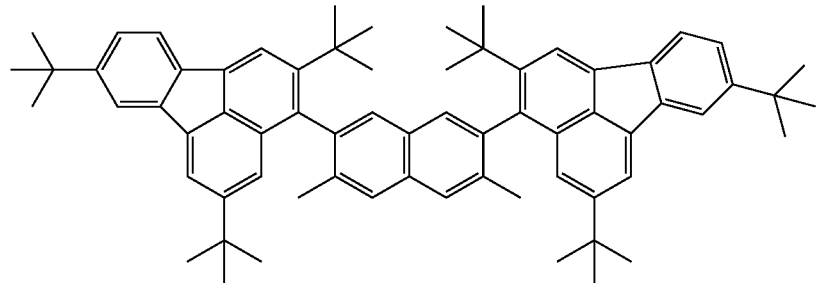

-continued

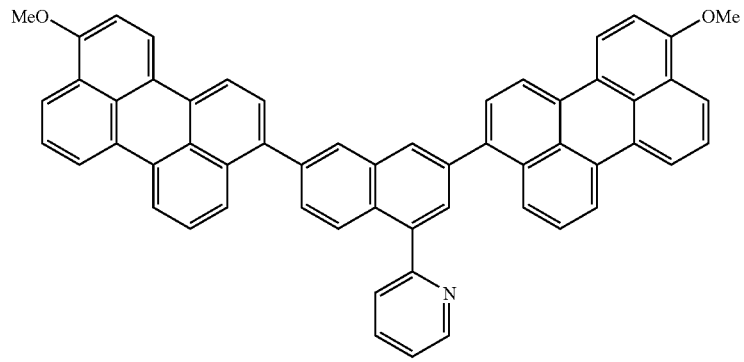

D-K-1

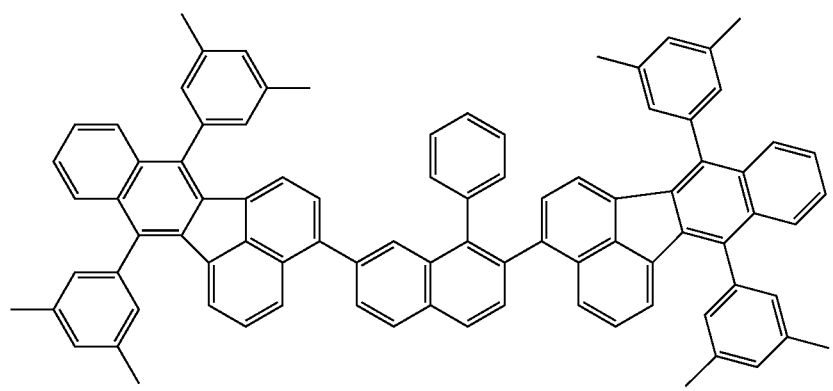

D-N-1

Next, the organic light-emitting device of the present invention will be described in detail.

The organic light-emitting device of the present invention is formed of an anode, a cathode, and a layer formed of an organic compound and interposed between the anode and the cathode. The layer formed of the organic compound contains the naphthalene compound of the present invention.

The organic light-emitting device of the present invention may have, between the cathode and the anode, another layer formed of another organic compound in addition to the above layer formed of the organic compound. The term "layer formed of an organic compound" herein employed refers to, for example, a hole-transporting layer, an electron-transporting layer, a hole injection layer, or a hole/exciton blocking layer for blocking holes and/or excitons.

The organic light-emitting device according to the present invention may appropriately have those other layers each formed of another organic compound.

In addition, the organic light-emitting device of the present invention is preferably an electroluminescent device that emits light by applying a voltage between an anode and a cathode.

Hereinafter, the organic light-emitting device of the present invention will be described in detail with reference to the drawings.

First, reference numerals used in the figures will be described. Reference numeral 1 denotes a substrate, reference numeral 2 denotes an anode, reference numeral 3 denotes a light-emitting layer, reference numeral 4 denotes a cathode, reference numeral 5 denotes a hole-transporting layer, reference numeral 6 denotes an electron-transporting layer, reference numeral 7 denotes a hole injection layer, reference numeral 8 denotes a hole/exciton blocking layer, and reference numerals 10, 20, 30, 40, 50, and 60 each denote an organic light-emitting device.

FIG. 1 is a schematic cross-sectional view illustrating a first embodiment of the organic light-emitting device of the present invention. In the organic light-emitting device 10 shown in FIG. 1, there are sequentially provided on a substrate 1, an anode 2, a light-emitting layer 3 and a cathode 4. The configuration of the organic light-emitting device 10 is useful when the light-emitting layer 3 is composed of a compound having all of hole transporting ability, electron transporting ability and light emitting ability. Further, the configuration is also useful when the light-emitting layer 3 is composed of a mixture of compounds having the characteristics of any one of hole transporting ability, electron transporting ability, and light emitting ability.

Figure 2:
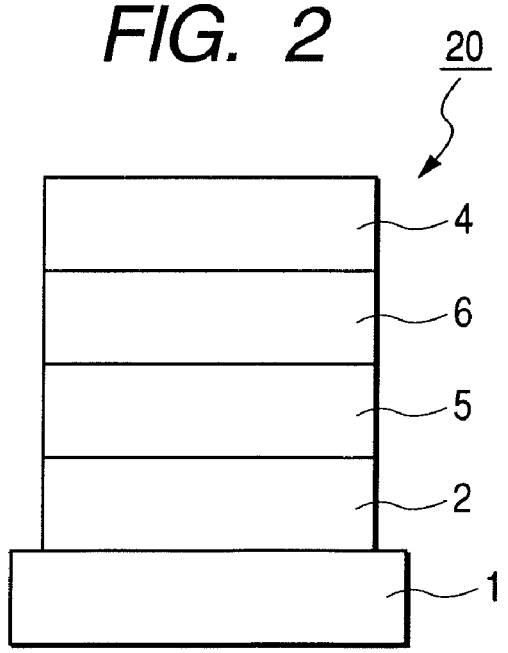
FIG. 2 is a cross-sectional view illustrating a second embodiment of the organic light-emitting device of the present invention.

FIG. 2 is a schematic cross-sectional view illustrating a second embodiment of the organic light-emitting device of the present invention. In the organic light-emitting device 20 shown in FIG. 2, there are sequentially provided on a substrate 1, an anode 2, a hole-transporting layer 5, an electron-transporting layer 6, and a cathode 4. The configuration of the organic light-emitting device 20 is useful when an organic compound having either one of hole transporting ability and electron transporting ability and an organic compound having only electron transporting ability or hole transporting ability are used in combination. Incidentally, in the organic light-emitting device 20 shown in FIG. 2, the hole-transporting layer 5 and the electron-transporting layer 6 each serve also as a light-emitting layer.

Figure 3:
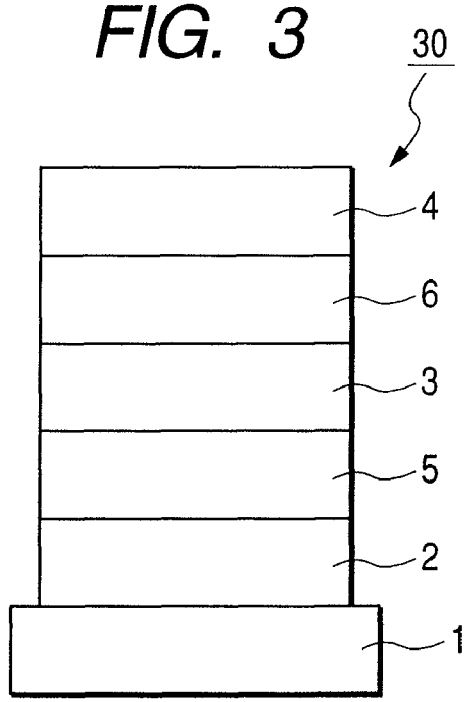
FIG. 3 is a cross-sectional view illustrating a third embodiment of the organic light-emitting device of the present invention.

FIG. 3 is a schematic cross-sectional view illustrating a third embodiment of the organic light-emitting device of the present invention. The organic light-emitting device 30 shown in FIG. 3 is different from the organic light-emitting device 20 shown in FIG. 2 in that a light-emitting layer 3 is additionally provided between a hole-transporting layer 5 and an electron-transporting layer 6. The organic light-emitting device 30 has a configuration in which the functions of carrier transportation and light emission are separated from each other, so that organic compounds having characteristics of hole-transporting property, electron-transporting property and light-emitting property, respectively, can suitably be combined and used. Therefore, since the degree of freedom in selecting materials can significantly be increased, and further since various organic compounds having different emission wavelengths can be used, a wide variety of emission hues can be provided. Further, it also becomes possible to effectively confine carriers or excitons in the light-emitting layer 3 at the central portion, thereby improving the emission efficiency.

Figure 4:
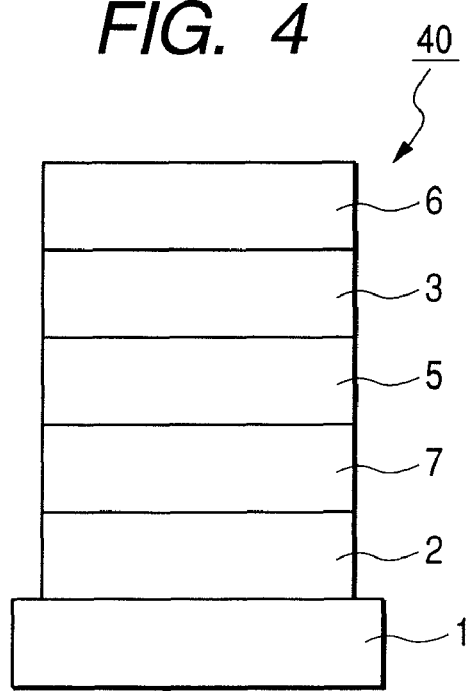
FIG. 4 is a cross-sectional view illustrating a fourth embodiment of the organic light-emitting device of the present invention.

FIG. 4 is a schematic cross-sectional view illustrating a fourth embodiment of the organic light-emitting device of the present invention. The organic light-emitting device 40 shown in FIG. 4 is different from the organic light-emitting device 30 shown in FIG. 3 in that a hole injection layer 7 is additionally provided between an anode 2 and a hole-transporting layer 5. In the organic light-emitting device 40, by additionally providing the hole injection layer 7, the adhesion between the anode 2 and the hole-transporting layer 5 or the hole injection property is improved, so that the driving voltage can be effectively reduced.

Figure 5:
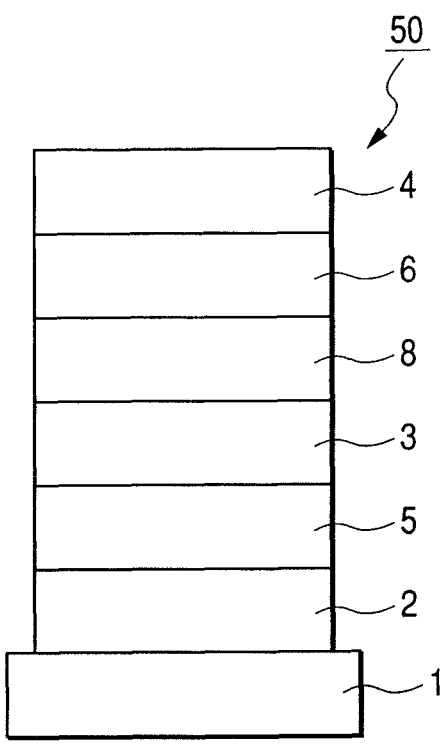
FIG. 5 is a cross-sectional view illustrating a fifth embodiment of the organic light-emitting device of the present invention.

FIG. 5 is a schematic cross-sectional view illustrating a fifth embodiment of the organic light-emitting device of the present invention. The organic light-emitting device 50 shown in FIG. 5 is different from the organic light-emitting device 30 shown in FIG. 3 in that a layer (hole/exciton blocking layer 8) for blocking holes or excitons from passing to a cathode 4 side is additionally provided between a light-emitting layer 3 and an electron-transporting layer 6. The configuration improves the emission efficiency of the organic light-emitting device 50 by using an organic compound with a significantly high ionization potential as the hole/exciton blocking layer 8.

Figure 6:
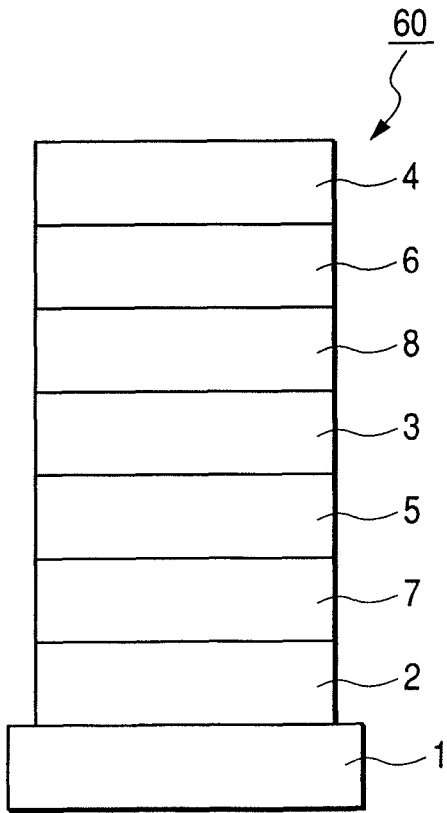
FIG. 6 is a cross-sectional view illustrating a sixth embodiment of the organic light-emitting device of the present invention.

FIG. 6 is a cross-sectional view illustrating a sixth embodiment of the organic light-emitting device of the present invention. The organic light-emitting device 60 shown in FIG. 6 is different from the organic light-emitting device 40 shown in FIG. 4 in that the hole/exciton-blocking layer 8 is additionally provided between the light-emitting layer 3 and the electron-transporting layer 6. By using an organic compound having an extremely high ionization potential as the hole/exciton blocking layer 8, the emission efficiency of the organic light-emitting device 60 can be improved.

FIGS. 1 to 6 merely show very basic device configurations and the configuration of the organic light-emitting device containing the naphthalene compound according to the present invention is not limited thereto. For example, it is possible to adopt various layer structures, such as one in which an insulating layer, an adhesive layer, or an interference layer is formed at an interface between an electrode and an organic layer. Further, a hole-transporting layer 5 is composed of two layers having different ionization potentials.

The naphthalene compound of the present invention has a large molecular weight and a high glass transition temperature. The fact means that an organic thin film formed of the naphthalene compound of the present invention has high thermal stability. Accordingly, the naphthalene compound of the present invention is considered to be useful as a material for an organic light-emitting device.

The naphthalene compound of the present invention can be used in any one of the embodiments shown in FIGS. 1 to 6. At that time, the naphthalene compound of the present invention may be used alone, or a plurality of compounds may be used in combination.

The naphthalene compound of the present invention can be used as a material for forming a layer formed of an organic compound such as any one of the light-emitting layer 3, the hole-transporting layer 5, the electron-transporting layer 6, the hole injection layer 7, and the hole/exciton blocking layer 8 shown in FIGS. 1 to 6. At that time, a layer may be formed of single kind of the naphthalene compound, or may be formed of a combination of two or more kinds of the naphthalene compounds.

When it is intended that the carrier transporting ability is exhibited at the maximum, or an appropriate energy gap is secured, the naphthalene compound of the present invention is preferably used as a material for forming the hole-transporting layer 5 and the electron-transporting layer 6 as carrier-transporting layers and the light-emitting layer 3.

In addition, the naphthalene compound of the present invention has a wide energy gap and therefore has high hole blocking property. Accordingly, the compound is useful as a material for forming the electron-transporting layer 6 (or the electron injection layer). In this case, the electron-transporting layer 6 (or the electron injection layer) may be formed of a plurality of layers including a layer formed only of an organic material and a layer obtained by doping an organic material with, for example, an alkali metal or an ion thereof, or an alkali metal salt.

The naphthalene compound of the present invention has a large $\pi$-electron system and a wide energy gap. Accordingly, the naphthalene compound of the present invention is preferably used as a material for forming a carrier-transporting layer. The naphthalene compound is more preferably used as a material for forming the electron-transporting layer 6 (or the electron injection layer) and a host for the light-emitting layer 3. The naphthalene compound is particularly preferably used as a material for forming the electron injection layer or a host for the light-emitting layer 3.

When the naphthalene compound of the present invention is used as a host for the light-emitting layer, the compound preferably has a wider energy gap than that of at least a guest as a light-emitting material. Therefore, as is the case with the naphthalene compound of the present invention, by introducing the fused ring aromatic hydrocarbon groups with four or more rings into such substitution positions (the 2- and 7-positions) where conjugated systems are not linked to each other, such a substituted compound can be used as a host material which is required to have a large energy gap. The naphthalene compound is particularly preferably used as a host for a blue-light-emitting layer which is required to have a larger energy gap out of such host materials.

Further, when the naphthalene compound of the present invention is used as a host for the light-emitting layer 3, the light-emitting material as a guest is not particularly limited, but is preferably a fluorescent material. In addition, when the naphthalene compound of the present invention is used as a host for the light-emitting layer 3, the content of the compound is preferably 50 wt % or more and 99.9 wt % or less, and more preferably 80 wt % or more and 99.9 wt % or less based on the total weight of all the materials constituting the light-emitting layer 3.

When the naphthalene compound of the present invention is used as a guest (light-emitting material) for the light-emitting layer 3, the content of the compound is preferably 0.1 wt % or more and 50 wt % or less, and more preferably 0.1 wt % or more and 20 wt % or less based on the total weight of all the materials constituting the light-emitting layer 3.

Although the naphthalene compound of the present invention can be used in any layer of the organic light-emitting device, a hitherto known hole-transporting material, matrix material, light-emitting material, electron-transporting material or the like can also be used together as needed.

Examples of those compounds are shown below. However the present invention is not limited to the examples.

Hole-Transporting Material
XA-1
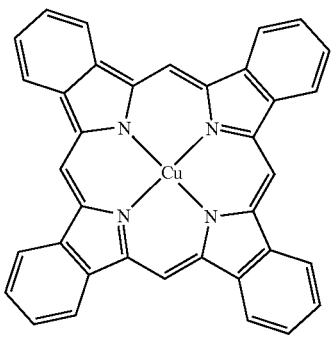
XA-6
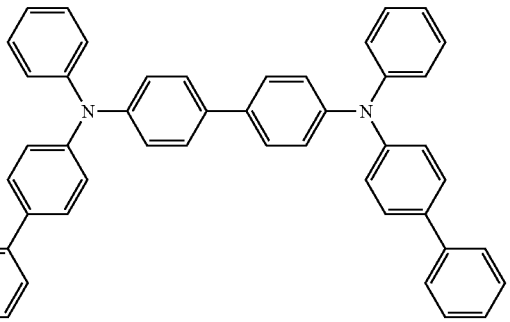
XA-2
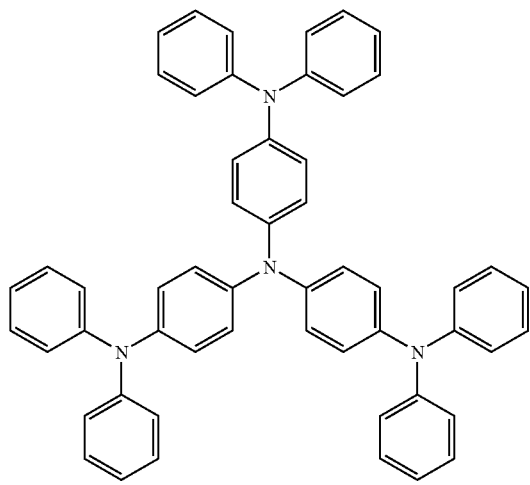
XA-7
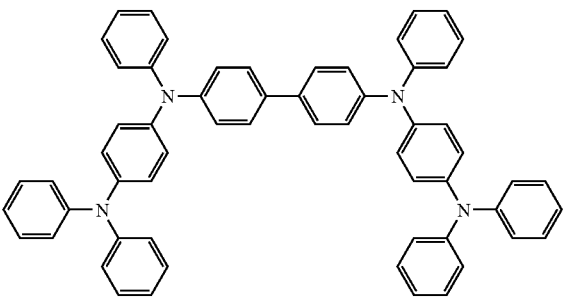
XA-3
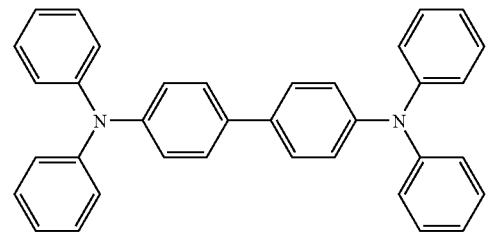
XA-8
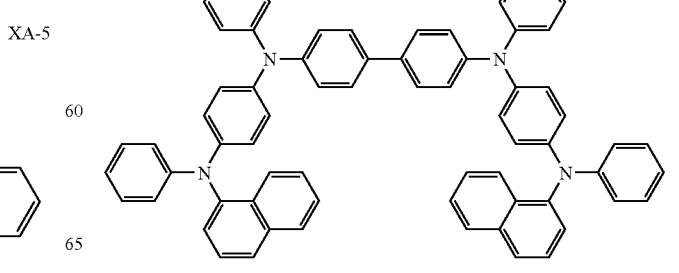
XA-4
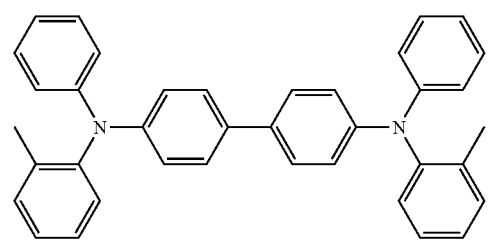
XA-5
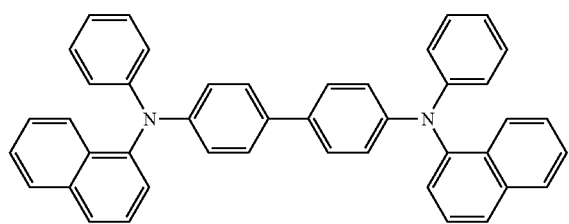
XA-9
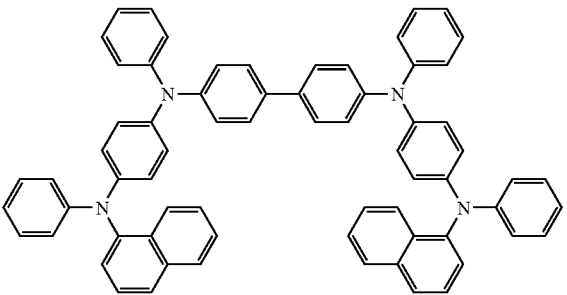

XA-10
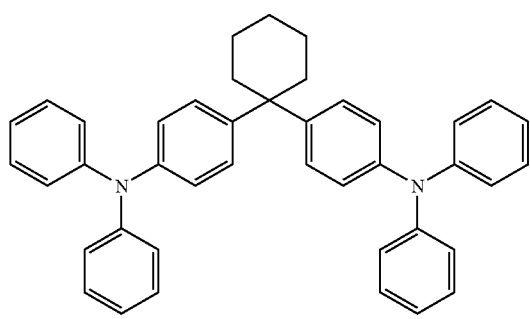
XA-11
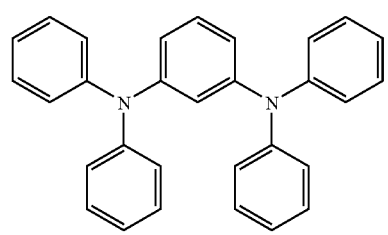
XA-12
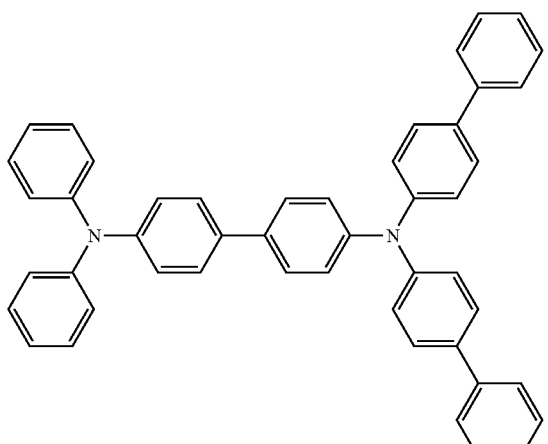
Matrix Material
XB-1
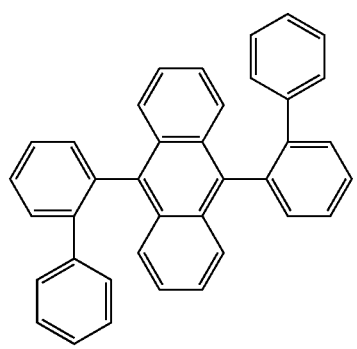
XB-2
XB-3
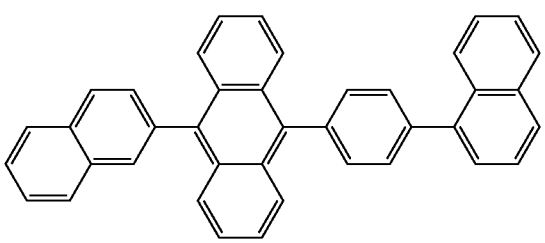
XB-4
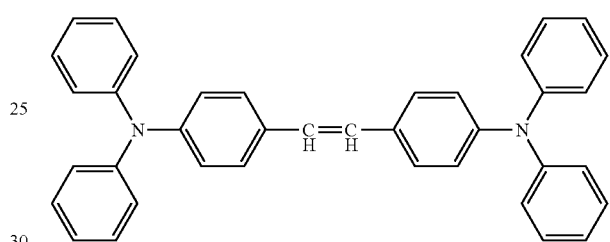
XB-5
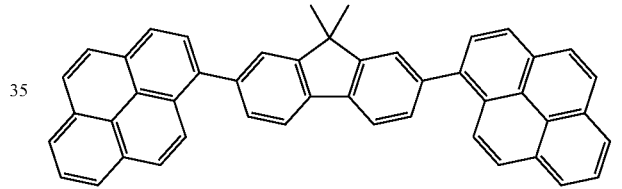
XB-6
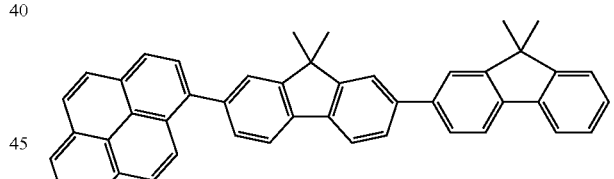
XB-7
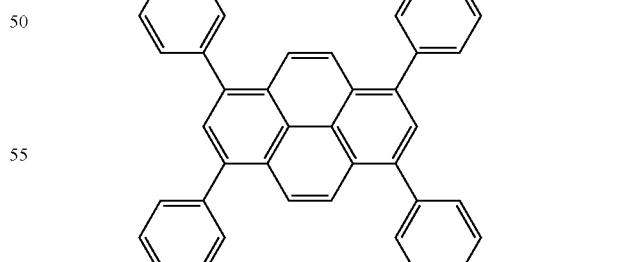
XB-8
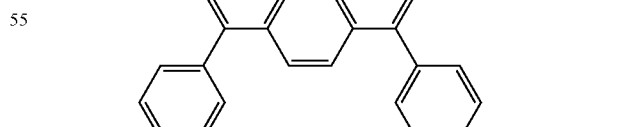

-continued
XB-9
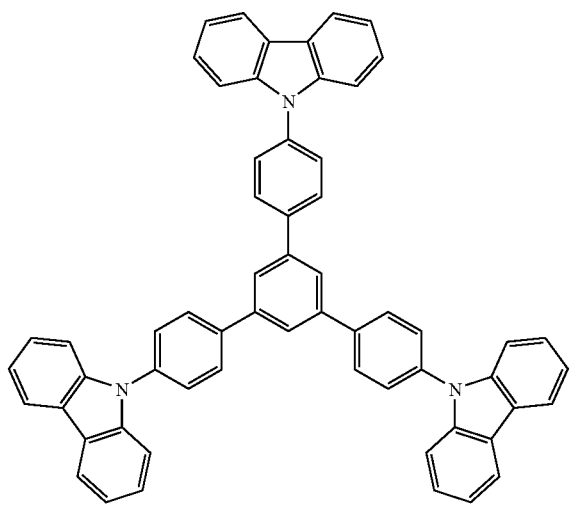
XB-10
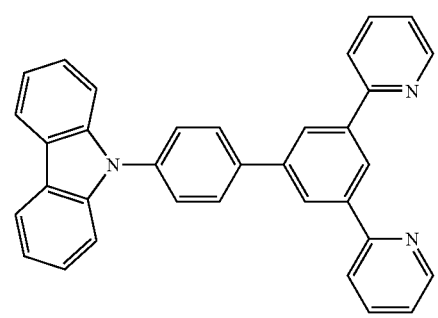
XB-11
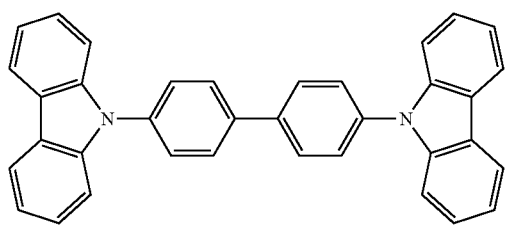
XB-12
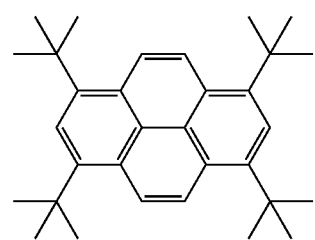
Light-Emitting Material
XC-1
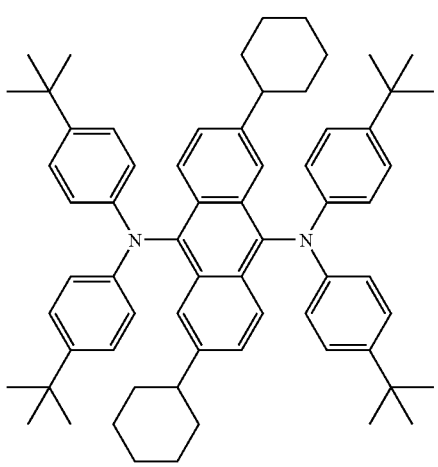
XC-2
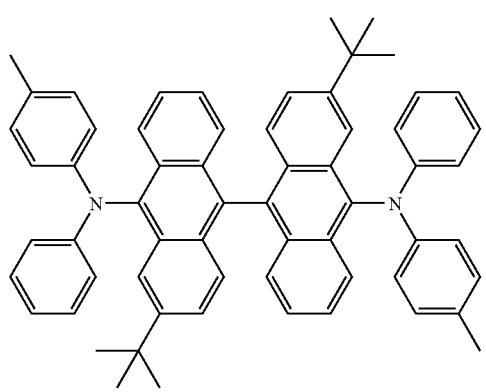
XC-3
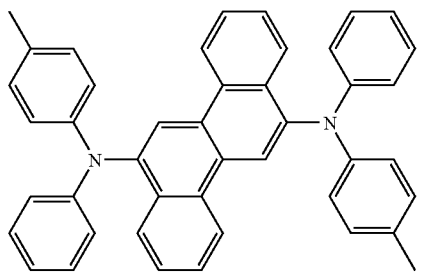
XC-4
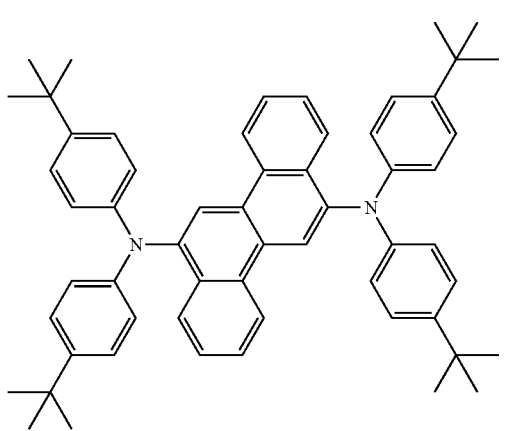

XC-5
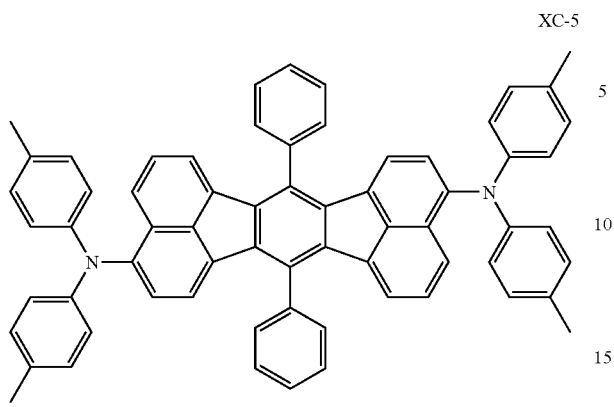
XC-6
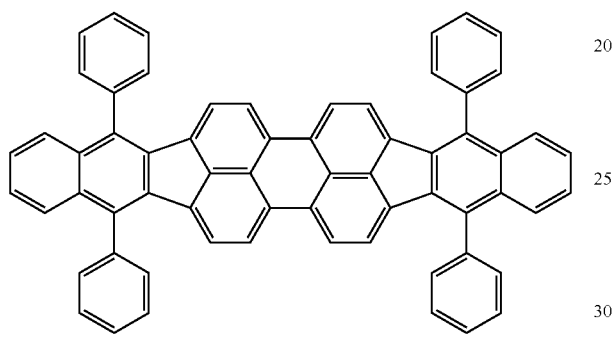
XC-7
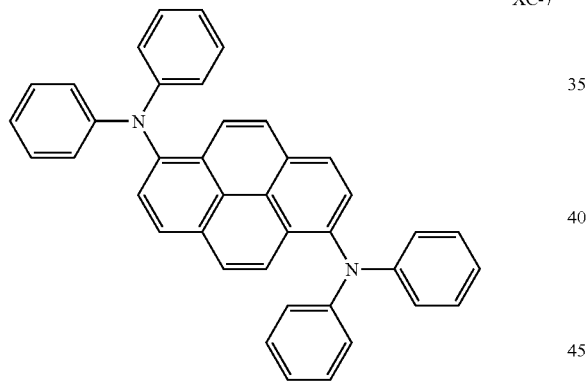
XC-8
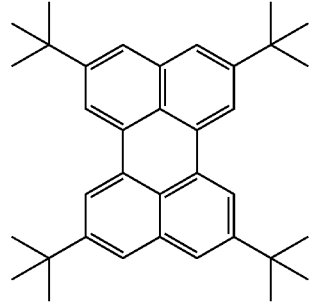
XC-9
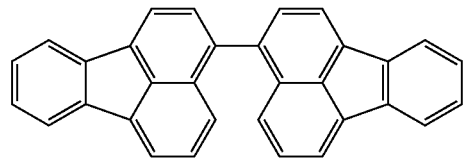
XC-10
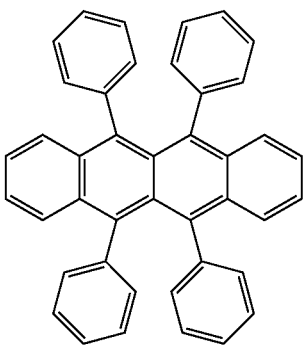
XC-11
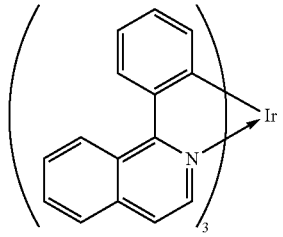
XC-12
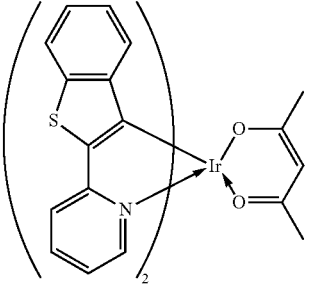
Electron-Transporting Material
XD-1
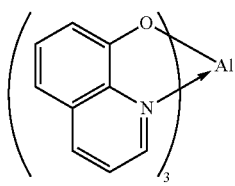
XD-2
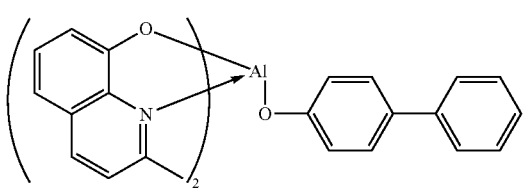
XD-3
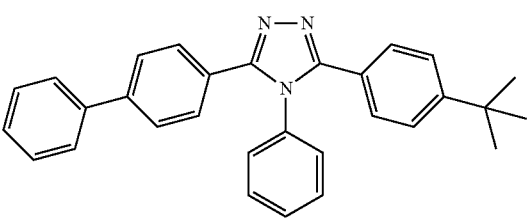

XD-4
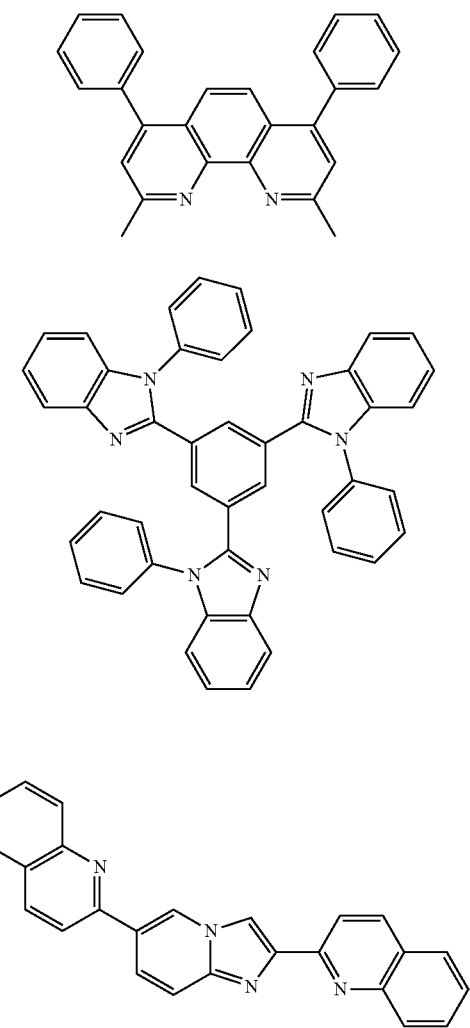
XD-5
XD-6
Polymer Material
XE-1
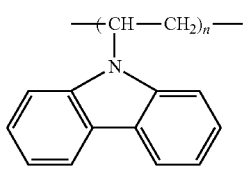
XE-2
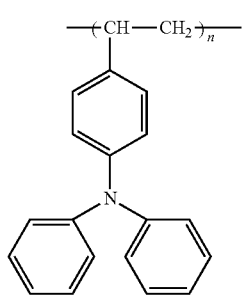
XE-3
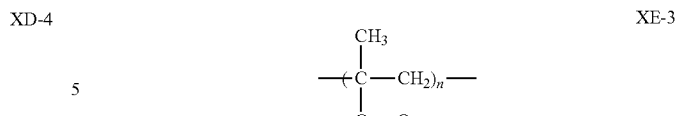
XE-4
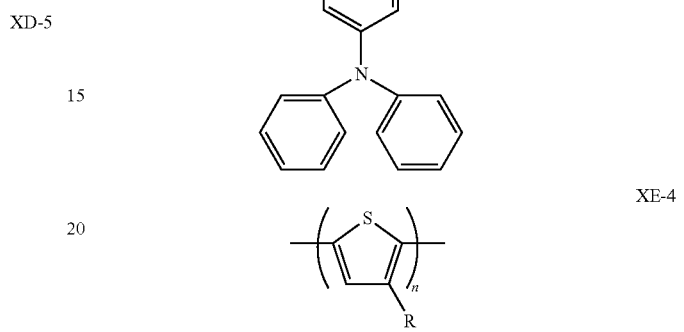
R: C6H13, C8H17, C12H25
XE-5
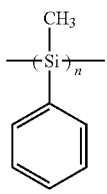
XE-6
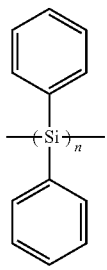
XE-7
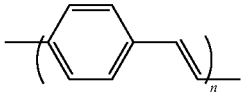
XE-8
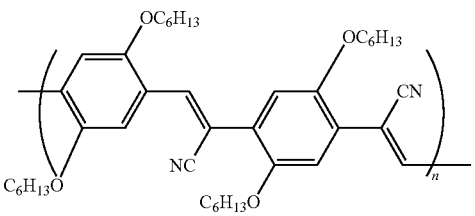
XE-9
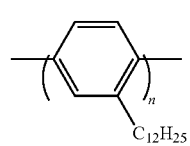

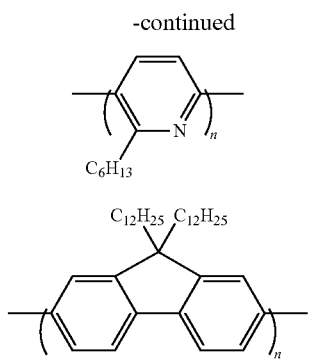

An anode material used for the organic light-emitting device of the present invention preferably has as large a work function as possible, and includes, for instance, an elemental metal such as gold, platinum, nickel, palladium, cobalt, selenium, and vanadium, an alloy thereof, and a metal oxide such as tin oxide, zinc oxide, indium tin oxide (ITO) and indium zinc oxide. Further, a conductive polymer such as polyaniline, polypyrrole, polythiophene and polyphenylene sulfide can be employed. These electrode materials can be used singly or in combination.

On the other hand, a cathode material used for the organic light-emitting device of the present invention preferably has a low work function, and include, for instance, an elemental metal such as lithium, sodium, potassium, cesium, calcium, magnesium, aluminum, indium, silver, lead, tin, and chromium. Alternatively, an alloy made of a plurality of the above metals can also be used. A metal oxide such as indium tin oxide (ITO) can be also utilized. In addition, the cathode may be either of a single layer configuration or of a multilayer configuration.

A substrate used for the organic light-emitting device of the present invention is not particularly limited, but an opaque substrate such as a metal substrate and a ceramic substrate or a transparent substrate such as glass, quartz, and a plastic sheet is used. Further, it is also possible to employ, for a substrate, a color filter film, a fluorescent color conversion filter film and a dielectric reflection film to thereby control the emission color.

Incidentally, after the organic light-emitting device has been produced, a protective layer or an encapsulation layer may further be provided, for the purpose of preventing contact with oxygen or moisture. Examples of such a protective layer include a diamond thin film; a film of an inorganic material such as a metal oxide and a metal nitride; a film of a polymer such as a fluororesin, poly-p-xylene, polyethylene, silicone resin, and polystyrene resin; and further a photocurable resin. Further, the produced device may also be covered with glass, a gas-impermeable film and a metal, or be packaged with a suitable encapsulation resin.

The layer formed of an organic compound which contains the naphthalene compound of the present invention, can be produced by, for example, a vacuum evaporation method, a casting method, a coating method, a spin coating method, or an ink-jet method.

EXAMPLES

Hereinafter, the present invention will be described specifically by way of Examples. However, the present invention is not limited to those Examples.

Example 1

(Synthesis of Exemplified Compound A-G-1)

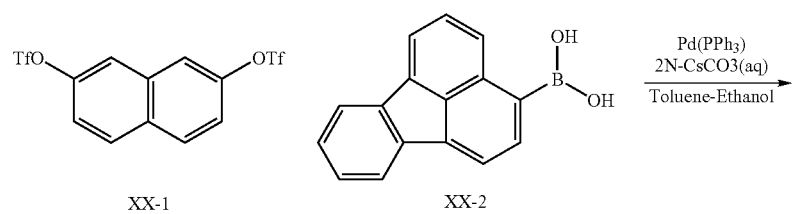

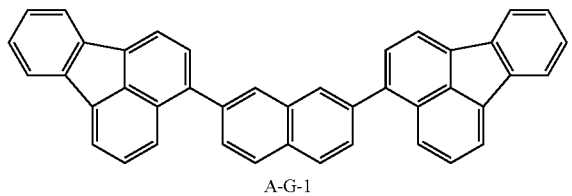

The below-mentioned reagents and solvents were placed in a 100 mL reaction vessel, and the solution was heated to 90° C. and was stirred at the temperature for 10 hours.
XX-2: 1 g (4.06 mmol)
XX-1: 780 mg (1.84 mmol)
Toluene: 20 mL
2N aqueous solution of cesium carbonate: 20 mL
Ethanol: 10 mL
Tetrakistriphenylphosphinepalladium[0]: 234 mg (0.203 mmol)

The solution was cooled to room temperature, and the precipitated crystal was filtrated, whereby a coarse crystal was obtained. The coarse crystal was recrystallized from o-dichlorobenzene, whereby 650 mg of Exemplified Compound A-G-1 was obtained (67% yield).

With electron ionization mass spectrometry (EI-MS), it was confirmed that the compound had an M+ of 528.

$^1$H-NMR(CDCl$_3$, 500 MHz)σ(ppm): 8.17(m, 2H), 8.10(d, 2H), 8.04(d, 2H), 8.03(d, 2H), 7.99(d, 2H), 7.95(m, 4H), 7.83(dd, 2H), 7.76(d, 2H), 7.65(dd, 2H), 7.41(m, 4H)

In addition, the glass transition temperature of Exemplified Compound A-G-1 was measured with a PYRIS-1 DSC manufactured by PerkinElmer, Inc. As a result, the glass transition temperature was 130° C.

Example 2

(Synthesis of Exemplified Compound B-F-1)

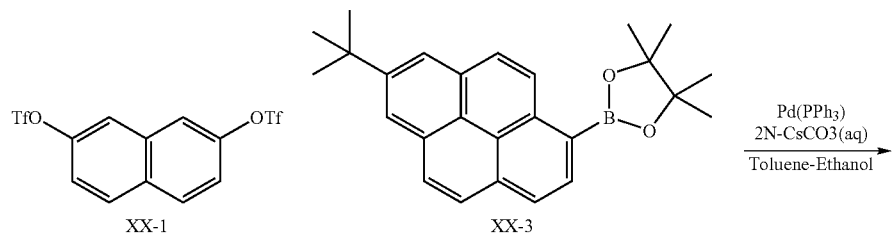

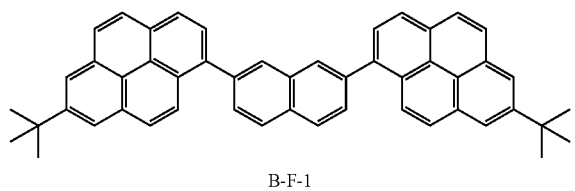

The below-mentioned reagents and solvents were placed in a 100 mL reaction vessel. The solution was heated to 90° C., and was stirred at the temperature for 10 hours.

XX-1: 2 g (4.72 mmol)
XX-3: 4 g (10.4 mmol)
Toluene: 30 mL
2N aqueous solution of cesium carbonate: 30 mL
Ethanol: 15 mL
Tetrakistriphenylphosphinepalladium[0]: 620 mg (0.54 mmol)

The solution was cooled to room temperature. After that, 50 ml of saturated brine were added to the solution, and the mixture was extracted with toluene (50 mL×3 times). The organic layer was washed with saturated brine, and was then dried with sodium sulfate. After the desiccant had been removed by filtration, the filtrate was concentrated. After that, the concentrate was separated and purified by silica gel column chromatography (mobile phase: toluene), whereby a colorless coarse crystal was obtained. The coarse crystal was recrystallized from a mixture of toluene and hexane, whereby 2 g of Exemplified Compound B-F-1 were obtained (yield=66%).

By EI-MS measurement, it was confirmed that the compound had an M+ of 640.

$^1$H-NMR(CDCl$_3$, 500 MHz)σ(ppm): 8.25(m, 6H), 8.21 (m, 4H), 8.16(d, 2H), 8.10(m, 6H), 8.04(d, 2H), 7.87(dd, 2H), 1.59(s, 18H)

In addition, the compound had a glass transition temperature of 167° C.

Exemplified Compound A-E-1 can be synthesized by following the same procedure as in Example 2 with the exception that XX-4 shown below is used instead of XX-3 used in Example 2.

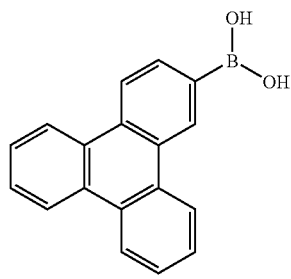

Exemplified Compound A-F-1 can be synthesized by following the same procedure as in Example 2 with the exception that XX-5 shown below is used instead of XX-3 used in Example 2.

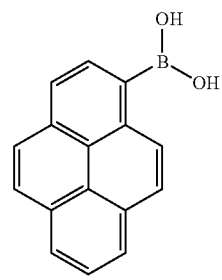

Exemplified Compound A-F-2 can be synthesized by following the same procedure as in Example 2 with the exception that XX-6 shown below is used instead of XX-3 used in Example 2.

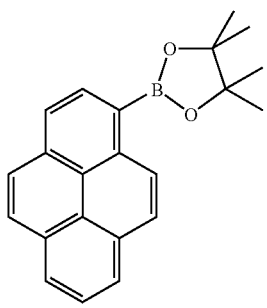

XX-6

Exemplified Compound A-K-1 can be synthesized by following the same procedure as in Example 2 with the exception that XX-7 shown below is used instead of XX-3 used in Example 2.

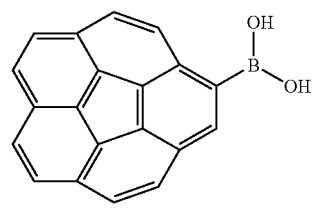

XX-7

Exemplified Compound A-Q-1 can be synthesized by following the same procedure as in Example 2 with the exception that XX-8 shown below is used instead of XX-3 used in Example 2.

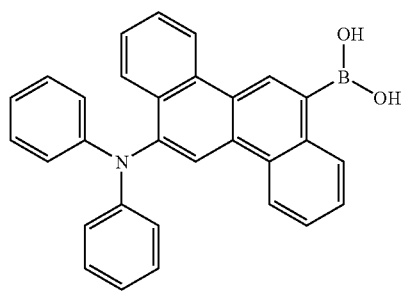

XX-8

Exemplified Compound B-C-1 can be synthesized by following the same procedure as in Example 2 with the exception that XX-9 shown below is used instead of XX-3 used in Example 2.

XX-9

Exemplified Compound B-F-2 can be synthesized by following the same procedure as in Example 2 with the exception that XX-10 shown below is used instead of XX-3 used in Example 2.

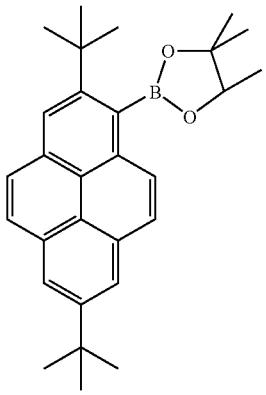

XX-10

Exemplified Compound B-F-3 can be synthesized by following the same procedure as in Example 2 with the exception that XX-11 shown below is used instead of XX-3 used in Example 2.

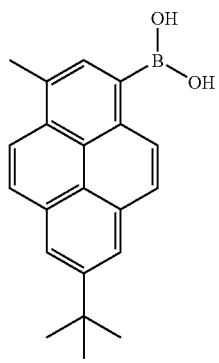

XX-11

Exemplified Compound B-G-5 can be synthesized by following the same procedure as in Example 2 with the exception that XX-12 shown below is used instead of XX-3 used in Example 2.

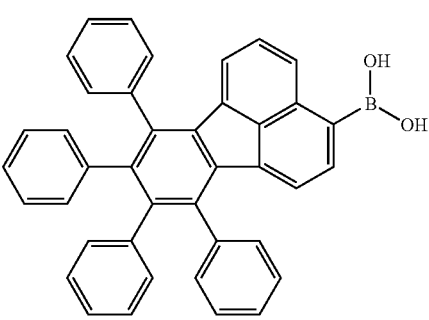

XX-12

Exemplified Compound B-N-1 can be synthesized by following the same procedure as in Example 2 with the exception that XX-13 shown below is used instead of XX-3 used in Example 2.

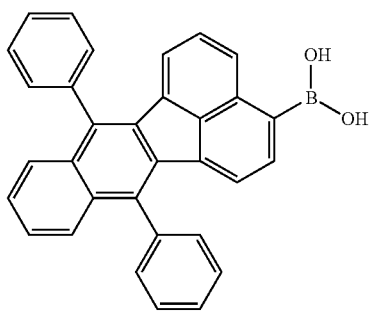

XX-13

Exemplified Compound C-F-1 can be synthesized by following the same procedure as in Example 2 with the exception that XX-14 shown below is used instead of XX-1 used in Example 2, and XX-5 is used instead of XX-3 used in Example 2.

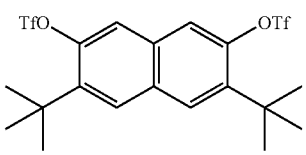

XX-14

Exemplified Compound D-F-1 can be synthesized by following the same procedure as in Example 2 with the exception that XX-14 is used instead of XX-1 used in Example 2.

Exemplified Compound D-F-2 can be synthesized by following the same procedure as in Example 2 with the exception that XX-15 shown below is used instead of XX-1 used in Example 2, and XX-16 shown below is used instead of XX-3 used in Example 2.

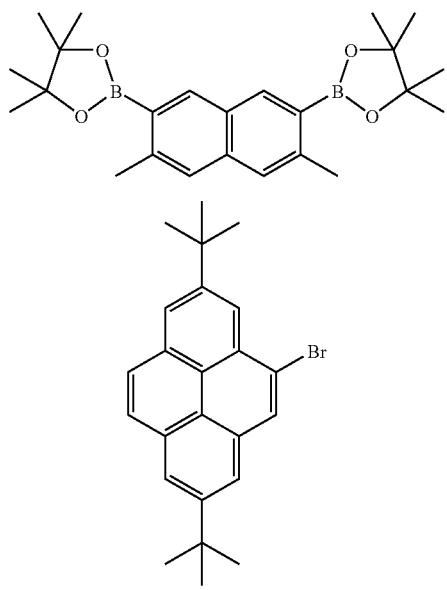

XX-15

XX-16

Example 3

An organic light-emitting device having three organic layers shown in FIG. 3 was produced.

On a glass substrate (substrate 1), a film of indium tin oxide (ITO) was formed in a thickness of 100 nm and patterned as the anode 2, whereby a transparent substrate having an ITO electrode was produced. On the transparent substrate with the ITO electrode, layers each including an organic compound and a cathode were continuously formed by vacuum evaporation using resistive heating. To be specific, first, as the hole-transporting layer 5, a film of α-NPD shown below was formed in a thickness of 40 nm by evaporation. Next, as the light-emitting layer 3, a film was formed by coevaporation of HOST-1 as a host and Exemplified Compound A-G-1 as a guest in such a manner that the content of Exemplified Compound A-G-1 was 10 wt % of the entirety of the light-emitting layer. At this time, the light-emitting layer had a thickness of 30 nm. Next, as the electron-transporting layer 6, a film of Bphen (manufactured by DOJINDO LABORATORIES) shown below was formed in a thickness of 30 nm by evaporation. Next, as a first metal electrode layer, a film of KF formed in a thickness of 1 nm by evaporation. Finally, as a second metal electrode layer, a film of Al was formed in a thickness of 130 nm by evaporation. The KF film and the Al film together function as the cathode 4.

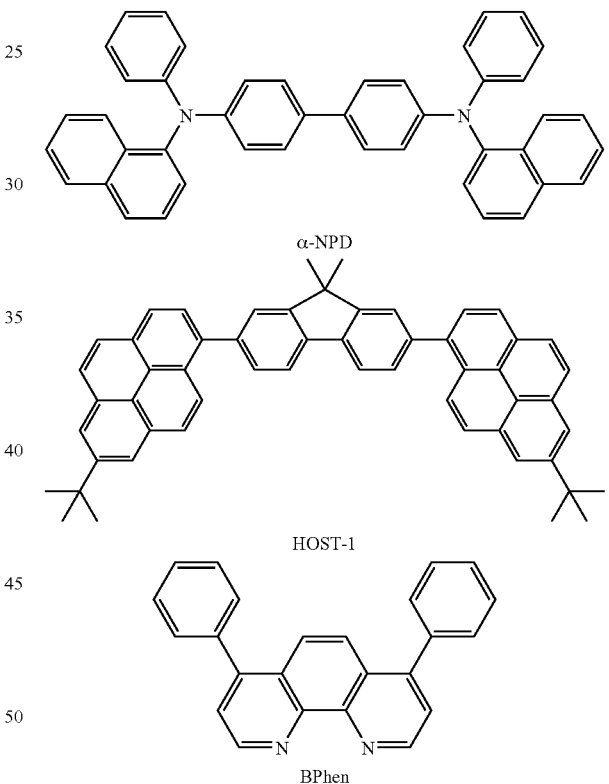

At this time, the pressure inside a vacuum chamber was set to $10^{-5}$ Pa, and an opposing electrode area was set to 3 mm$^2$. By the above described procedure, the organic light-emitting device was obtained.

For the characteristics of the thus obtained organic light-emitting device, the current-voltage characteristics were measured with a pico-amp meter (Hewlett Packard 4140B), and the emission luminance was measured with a BM7 manufactured by TOPCON CORPORATION.

When a voltage was applied to the device of this example in a nitrogen atmosphere for 100 hours, it was observed that the device satisfactorily continued to emit light. The emission material of Exemplified Compound A-G-1 was confirmed to be useful as a blue-light-emitting material.

Example 4

On a glass substrate (substrate 1), a film of indium tin oxide (ITO) was formed in a thickness of 100 nm and patterned as the anode 2, whereby a transparent substrate having an ITO electrode was produced. On the transparent substrate with the ITO electrode, layers each including an organic compound and a cathode were continuously formed by vacuum evaporation using resistive heating. To be specific, first, as the hole-transporting layer 5, a film of HTL-1 shown below was formed in a thickness of 25 nm by evaporation. Next, as the light-emitting layer 3, a film was formed by coevaporation of Exemplified Compound B-F-1 as a host and GUEST-2 shown below as a guest in such a manner that the content of GUEST-2 was 5 wt % of the entirety of the light-emitting layer. At this time, the light-emitting layer had a thickness of 30 nm. Next, as the electron-transporting layer 6, a film of Bphen (manufactured by DOJINDO LABORATORIES) shown below was formed in a thickness of 30 nm by evaporation. Next, as a first metal electrode layer, a film of KF formed in a thickness of 1 nm by evaporation. Finally, as a second metal electrode layer, a film of Al was formed in a thickness of 130 nm by evaporation. The KF film and the Al film together function as the cathode 4.

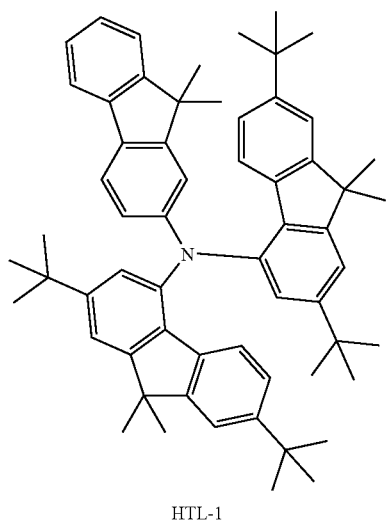

HTL-1

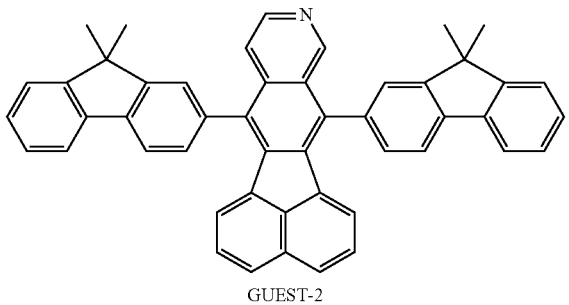

GUEST-2

At this time, the pressure inside a vacuum chamber was set to $10^{-5}$ Pa, and an opposing electrode area was set to 3 mm$^2$. By the above described procedure, the organic light-emitting device was obtained.

The thus obtained device was evaluated in the same manner as in Example 3. As a result, the device had an emission efficiency of 5.3 cd/A (400 cd/m$^2$). In addition, when the device was continuously energized at 30 mA/cm$^2$, the time it takes for the initial luminance to decrease to its half value was 600 hours.

It was confirmed from the above results that the naphthalene compound of the present invention is useful as a host material.

Example 5

A device was produced by following the same procedure as in Example 3 with the exception that GUEST-1 was used instead of Exemplified Compound A-G-1 as a guest for the light-emitting layer 3, and Exemplified Compound B-F-1 was used instead of Bphen as the electron-transporting layer 6.

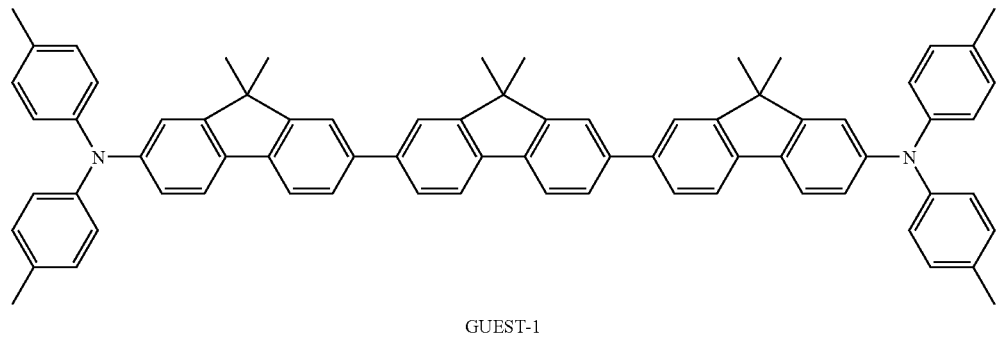

GUEST-1

When a voltage was applied to the thus obtained device in a nitrogen atmosphere for 100 hours, it was observed that the device satisfactorily continued to emit light. Since Exemplified Compound B-F-1 has a glass transition temperature of 167° C., which is higher than the glass transition temperature (60° C.) of Bphen, a thin film formed of Exemplified Compound B-F-1 has high thermal stability as compared to that of a thin film formed of Bphen. Accordingly, it can be said that Exemplified Compound B-F-1 is a material useful in preventing the degradation of an organic light-emitting device which is considered to be attributable to the crystallization of an organic thin film. In addition, Exemplified Compound B-F-1 is a material useful also in driving an organic light-emitting device at high temperatures.

Example 6

(Synthesis of Exemplified Compound A-F-1)

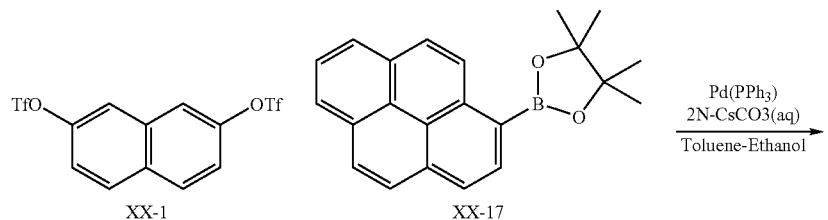

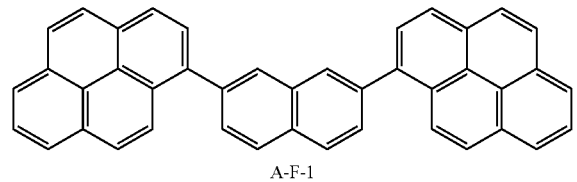

A-F-1

The below-mentioned reagents and solvents were placed in a 100 mL reaction vessel, and the solution was heated to 90° C. and was stirred at the temperature for 10 hours.
XX-1: 2 g (4.72 mmol)
XX-17: 3.4 g (10.4 mmol)
Toluene: 30 mL
2N aqueous solution of cesium carbonate: 30 mL
Ethanol: 15 mL
Tetrakistriphenylphosphinepalladium[0]: 620 mg (0.54 mmol)

After the solution was cooled to room temperature, the formed precipitate was separated from the solution by filtration. The precipitate was washed sequentially with water, ethanol and toluene to obtain a colorless coarse crystal. The coarse crystal was recrystallized from chlorobenzene, whereby 1.5 g of Exemplified Compound A-F-1 was obtained (60% yield).

With electron ionization mass spectrometry (EI-MS), it was confirmed that the compound had an M+ of 528.

$^1$H-NMR(CDCl$_3$,500 MHz)σ(ppm):8.29(d,2H),8.28 (d,2H), 8.22-8.11(m,14H),8.07-8.01(m,4H),7.87(dd,2H)

In addition, the glass transition temperature of this compound was 130° C.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-062188, filed Mar. 12, 2007, which is hereby incorporated by reference herein in its entirety.

What is claimed is:

1. An organic light-emitting device, comprising:
an anode;
a cathode; and
a light-emitting layer comprising an organic compound interposed between the anode and the cathode,
wherein the light-emitting layer comprises a host and a guest,
wherein the host comprises a naphthalene compound represented by the general formula (1):

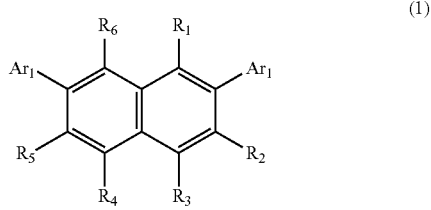

wherein $Ar_1$'s each represent a substituted or unsubstituted fluoranthenyl group, and $R_1$, $R_2$, $R_3$, $R_4$, $R_5$, and $R_6$ each represent, independently of one another, a hydrogen atom, a halogen atom, an alkyl group having 1 to 20 carbon atoms, a substituted or unsubstituted aryl group, or a substituted or unsubstituted heterocyclic group, and
wherein the guest is a compound represented by the following structural formula:

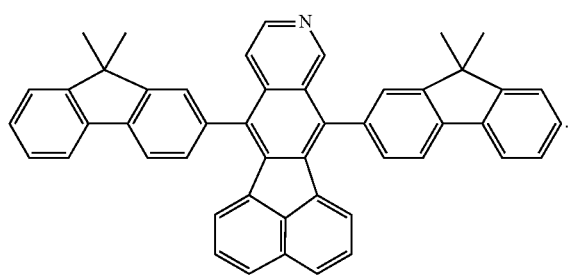
2. The organic light-emitting device according to claim 1, which is an electroluminescent device that emits light by applying a voltage between the anode and the cathode.
3. The organic light-emitting device according to claim 1, wherein the host is represented by the following structural formula:
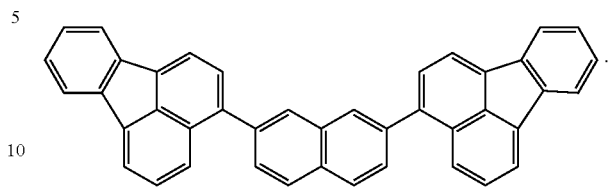
* * * * *